US009944918B2

(12) United States Patent
Venditti et al.

(10) Patent No.: US 9,944,918 B2
(45) Date of Patent: *Apr. 17, 2018

(54) SYNTHETIC METHYLMALONYL-COA MUTASE TRANSGENE FOR THE TREATMENT OF MUT CLASS METHYLMALONIC ACIDEMIA (MMA)

(71) Applicant: The United States of America, as represented by the Secretary, Dept. of Health and Human Services, Washington, DC (US)

(72) Inventors: Charles P. Venditti, Potomac, MD (US); Randy J. Chandler, Washington, DC (US)

(73) Assignee: The United States of America, as represented by the Secretary, Dept. of Health & Human Services, Washington, DC (US)

( * ) Notice: Subject to any disclaimer, the term of this patent is extended or adjusted under 35 U.S.C. 154(b) by 39 days.

This patent is subject to a terminal disclaimer.

(21) Appl. No.: 15/070,787

(22) Filed: Mar. 15, 2016

(65) Prior Publication Data
US 2017/0067042 A1    Mar. 9, 2017

Related U.S. Application Data

(63) Continuation-in-part of application No. 14/773,885, filed as application No. PCT/US2014/028045 on Mar. 14, 2014.

(60) Provisional application No. 61/792,081, filed on Mar. 15, 2013.

(51) Int. Cl.
*A61K 48/00* (2006.01)
*C07H 21/04* (2006.01)
*C12N 15/74* (2006.01)
*C12N 9/90* (2006.01)
*A61K 38/00* (2006.01)

(52) U.S. Cl.
CPC ........ *C12N 9/90* (2013.01); *C12Y 504/99002* (2013.01); *A61K 38/00* (2013.01)

(58) Field of Classification Search
None
See application file for complete search history.

(56) References Cited

U.S. PATENT DOCUMENTS

| 7,358,351 | B2 | 4/2008 | St. Croix et al. |
| 7,745,391 | B2* | 6/2010 | Mintz ..................... G06F 19/24 |
| | | | 514/19.3 |
| 8,999,380 | B2 | 4/2015 | Bancel et al. |
| 2016/0040150 | A1* | 2/2016 | Venditti ................... C12N 9/90 |
| | | | 514/44 R |

FOREIGN PATENT DOCUMENTS

WO    WO 2013/151666    10/2013

OTHER PUBLICATIONS

Chandler et al. FASEB J. 2009;23:1252-61.*
Chandler et al. Mole Ther 2010;18:11-16.*
Bahr et al. (2004) GenBank Accession No. CR857121.1.
International Search Report and Written Opinion dated Sep. 16, 2014 for PCT/US2014/028045.
Ledley et al. (1988) Proc. Natl. Sci. USA 85:3518-3521 "Molecular cloning of L-methylmalonyl-CoA mutase: Gene transfer and analysis of mut cell lines".
Senac et al. (2012) Gene Therapy 19:385-391 "Gene therapy in a murine model of methylmalonic academia using rAAV9-mediated gene delivery".
Carrillo-Carrasco et al. (2010) Human Gene Therapy 21:1147-1154 "Liver-Directed Recombinant Adeno-Associated Viral Gene Delivery Rescues a Lethal Mouse Model of Methylmalonic Acidemia and Provides Long-Term Phenotypic Correction".
Händel et al. (2011) Human Gene Therapy 23:321-329 "Versatile and Efficient Genome Editing in Human Cells by Combining Zinc-Finger Nucleases With Adeno-Associated Viral Vectors".

* cited by examiner

*Primary Examiner* — Qian Janice Li
(74) *Attorney, Agent, or Firm* — Swanson & Bratschun, L.L.C.

(57) ABSTRACT

Synthetic polynucleotides encoding human methylmalonyl-CoA mutase (synMUT) and exhibiting augmented expression in cell culture and/or in a subject are described herein. An adeno-associated viral (AAV) gene therapy vector encoding synMUT under the control of a liver-specific promoter (AAV2/8-HCR-hAAT-synMUT-RBG) successfully rescued the neonatal lethal phenotype displayed by methylmalonyl-CoA mutase-deficient mice, lowered circulating methylmalonic acid levels in the treated animals, and resulted in prolonged hepatic expression of the product of synMUT transgene in vivo, human methylmalonyl-CoA mutase (MUT).

11 Claims, 29 Drawing Sheets

Figure 1

_Homo sapiens_ [gbpri]: 93487 CDS's (40662582 codons)

fields: [triplet] [frequency: per thousand] ([number])

```
UUU 17.6(714298)   UCU 15.2(618711)   UAU 12.2(495699)   UGU 10.6(430311)
UUC 20.3(824692)   UCC 17.7(718892)   UAC 15.3(622407)   UGC 12.6(513028)
UUA  7.7(311881)   UCA 12.2(496448)   UAA  1.0( 40285)   UGA  1.6( 63237)
UUG 12.9(525688)   UCG  4.4(179419)   UAG  0.8( 32109)   UGG 13.2(535595)

CUU 13.2(536515)   CCU 17.5(713233)   CAU 10.9(441711)   CGU  4.5(184609)
CUC 19.6(796638)   CCC 19.8(804620)   CAC 15.1(613713)   CGC 10.4(423516)
CUA  7.2(290751)   CCA 16.9(688038)   CAA 12.3(501911)   CGA  6.2(250760)
CUG 39.6(1611801)  CCG  6.9(281570)   CAG 34.2(1391973)  CGG 11.4(464485)

AUU 16.0(650473)   ACU 13.1(533609)   AAU 17.0(689701)   AGU 12.1(493429)
AUC 20.8(846466)   ACC 18.9(768147)   AAC 19.1(776603)   AGC 19.5(791383)
AUA  7.5(304565)   ACA 15.1(614523)   AAA 24.4(993621)   AGA 12.2(494682)
AUG 22.0(896005)   ACG  6.1(246105)   AAG 31.9(1295568)  AGG 12.0(486463)

GUU 11.0(448607)   GCU 18.4(750096)   GAU 21.8(885429)   GGU 10.8(437126)
GUC 14.5(588138)   GCC 27.7(1127679)  GAC 25.1(1020595)  GGC 22.2(903565)
GUA  7.1(287712)   GCA 15.8(643471)   GAA 29.0(1177632)  GGA 16.5(669873)
GUG 28.1(1143534)  GCG  7.4(299495)   GAG 39.6(1609975)  GGG 16.5(669768)
```

Coding GC 52.27% 1st letter GC 55.72% 2nd letter GC 42.54% 3rd letter GC 58.55%

Figure 2

SEQ ID NO:1

```
ATGCTGAGAGCCAAAAACCAGCTGTTCCTGCTGAGCCCCCACTATCTGAGACAGGTCAAAGAAAGTTCCG
GGAGTAGACTGATCCAGCAGAGACTGCTGCACCAGCAGCAGCCACTGCATCCTGAGTGGGCCGCTCTGGC
CAAGAAACAGCTGAAGGGCAAAAACCCAGAAGACCTGATCTGGCACACTCCAGAGGGGATTTCAATCAAG
CCCCTGTACAGCAAAAGGGACACTATGGATCTGCCAGAGGAACTGCCAGGAGTGAAGCCTTTCACCCGCG
GACCTTACCCAACTATGTATACCTTTCGACCCTGGACAAATTCGGCAGTACGCCGGCTTCAGTACTGTGGA
GGAATCAAACAAGTTTTATAAGGACAACATCAAGGCTGGACAGCAGGGCCTGAGTGTGGCATTCGATCTG
GCCACACATCGCGGCTATGACTCAGATAATCCCAGAGTCAGGGGGACGTGGGAATGGCAGGAGTCGCTA
TCGACACAGTGGAAGATACTAAGATTCTGTTCGATGGAATCCCTCTGGAGAAAATGTCTGTGAGTATGAC
AATGAACGGCGCTGTCATTCCCGTGCTGGCAAACTTCATCGTCACTGGCGAGGAACAGGGGGTGCCTAAG
GAAAAACTGACCGGCACAATTCAGAACGACATCCTGAAGGAGTTCATGGTGCGGAATACTTACATTTTTC
CCCCTGAACCATCCATGAAAATCATTGCCGATATCTTCGAGTACACCGCTAAGCACATGCCCAAGTTCAA
CTCAATTAGCATCTCCGGGTATCATATGCAGGAAGCAGGAGCCGACGCTATTCTGGAGCTGGCTTACACC
CTGGCAGATGGCCTGGAATATTCTCGAACCGGACTGCAGGCAGGCCTGACAATCGACGAGTTCGCTCCTA
GACTGAGTTCTTTTGGGGAATTGGCATGAACTTTTACATGGAGATCGCCAAGATGAGGGCTGGCCGGAG
ACTGTGGGCACACCTGATCGAGAAGATGTTCCAGCCTAAGAACTCTAAGAGTCTGCTGCTGCGGGCCCAT
TGCCAGACATCCGGCTGGTCTCTGACTGAACAGGACCCATATAACAATATTGTCAGAACCGCAATCGAGG
CAATGGCAGCCGTGTTCGGAGGAACCCAGAGCCTGCACACAAACTCCTTTGATGAGGCCCTGGGGCTGCC
TACCGTGAAGTCTGCTAGGATTGCACGCAATACACAGATCATTATCCAGGAGGAATCCGGAATCCCAAAG
GTGGCCGATCCCTGGGGAGGCTCTTACATGATGGAGTGCCTGACAAACGACGTGTATGATGCTGCACTGA
AGCTGATTAATGAAATCGAGGAAATGGGGGGAATGGCAAAGGCCGTGGCTGAGGGCATTCCAAAACTGAG
GATCGAGGAATGTGCAGCTAGGCGCCAGGCACGAATTGACTCAGGAAGCGAAGTGATCGTCGGGGTGAAT
AAGTACCAGCTGGAGAAAGAAGACGCAGTCGAAGTGCTGGCCATCGATAACACAAGCGTGCGCAATCGAC
AGATTGAGAAGCTGAAGAAAATCAAAAGCTCCCGCGATCAGGCACTGGCCGAACGATGCCTGGCAGCCCT
GACTGAGTGTGCTGCAAGCGGGGACGGAAACATTCTGGCTCTGGCAGTCGATGCCTCCCGGGCTAGATGC
ACTGTGGGGAAATCACCGACGCCCTGAAGAAAGTCTTCGGAGAGCACAAGGCCAATGATCGGATGGTGA
GCGGCGCTTATAGACAGGAGTTCGGGGAATCTAAAGAGATTACCAGTGCCATCAAGAGGGTGCACAAGTT
CATGGAGAGAGAAGGGCGACGGCCCAGGCTGCTGGTGGCAAAGATGGGACAGGACGGACATGATCGCGGA
GCAAAAGTCATTGCCACCGGGTTCGCTGACCTGGGATTTGACGTGGATATCGGCCCTCTGTTCCAGACAC
CACGAGAGGTCGCACAGCAGGCAGTCGACGCTGATGTGCACGCAGTCGGAGTGTCCACTCTGGCAGCTGG
CCATAAGACCCTGGTGCCTGAACTGATCAAAGAGCTGAACTCTCTGGGCAGACCAGACATCCTGGTCATG
TGCGGCGGCGTGATCCCACCCCAGGATTACGAATTCCTGTTTGAGGTCGGGGTGAGCAACGTGTTCGGAC
CAGGAACCAGGATCCCTAAGGCCGCAGTGCAGGTCCTGGATGATATTGAAAAGTGTCTGGAAAAGAAACA
GCAGTCAGTGTAA
```

Figure 3

SEQ ID NO:2

```
  1  mlraknqlfl isphylrqvk essgsrliqq rllhqqqplh pewaalakkq lkgknpedli
 61  whtpegisik plyskrdtmd lpeelpgvkp ftrgpyptmy tfrpwtirqy agfstveesn
121  kfykdnikag qqglsvafdl athrgydsdn prvrgdvgma gvaidtvedt kilfdgiple
181  kmsvsmtmng avipvlanfi vtgeeqgvpk ekltgtiqnd ilkefmvrnt yifppepsmk
241  iiadifeyta khmpkfnsis isgyhmqeag adailelayt ladgleysrt glqagltide
301  faprlsffwg igmnfymeia kmragrrlwa hliekmfqpk nskslllrah cqtsgwslte
361  qdpynnivrt aieamaavfq gtqsihtnsf dealglptvk sariarntqi iiqeesqipk
421  vadpwggsym mecltndvyd aalklineie emggmakava egipklriee caarrqarid
481  sgsevivgvn kyqlekedav evlaidntsv rnrqieklkk ikssrdqala ehclaaltec
541  aasgdgnila lavdasrarc tvgeitdalk kvfgehkand rmvsgayrqe fgeskeitsa
601  ikrvhkfmer egrrprllva kmgqdghdrg akviatgfad lgfdvdigpl fqtprevaqq
661  avdadvhavg vstlaaghkt lvpelikeln slgrpdilvm cggvippqdy eflfevgvsn
721  vfgpgtripk aavqvlddie kclekkqqsv
```

SEQ ID NO:3

```
ATGTTAAGAGCTAAGAATCAGCTTTTTTTACTTTCACCTCATTACCTGAGGCAGGTAAAAGAATCATCAG
GCTCCAGGCTCATACAGCAACGACTTCTACACCAGCAACAGCCCCTTCACCCAGAATGGGCTGCCCTGGC
TAAAAAGCAGCTGAAAGGCAAAAACCCAGAAGACCTAATATGGCACACCCCGGAAGGGATCTCTATAAAA
CCCTTGTATTCCAAGAGAGATACTATGGACTTACCTGAAGAACTTCCAGGAGTGAAGCCATTCACACGTG
GACCATATCCTACCATGTATACCTTTAGGCCCTGGACCATCCGCCAGTATGCTGGTTTTAGTACTGTGGA
AGAAAGCAATAAGTTCTATAAGGACAACATTAAGGCTGGTCAGCAGGGATTATCAGTTGCCTTTGATCTG
GCGACACATCGTGGCTATGATTCAGACAACCCTCGAGTTCGTGGTGATGTTGGAATGGCTGGAGTTGCTA
TTGACACTGTGGAAGATACCAAAATTCTTTTTGATGGAATTCCTTTAGAAAAAATGTCAGTTTCCATGAC
TATGAATGGAGCAGTTATTCCAGTTCTTGCAAATTTTATAGTAACTGGAGAAGAACAAGGTGTACCTAAA
GAGAAGCTTACTGGTACCATCCAAAATGATATACTAAAGGAATTTATGGTTCGAAATACATACATTTTTC
CTCCAGAACCATCCATGAAAATTATTGCTGACATATTTGAATATACAGCAAAGCACATGCCAAAATTTAA
TTCAATTTCAATTAGTGGATACCATATGCAGGAAGCAGGGGCTGATGCCATTCTGGAGCTGGCCTATACT
TTAGCAGATGGATTGGAGTACTCTAGAACTGGACTCCAGGCTGGCCTGACAATTGATGAATTTGCACCAA
CGTTGTCTTTCTTCTGGGGAATTGGAATGAATTTCTATATGGAAATAGCAAAGATGAGAGCTGGTAGAAG
ACTCTGGGCTCACTTAATAGAGAAAATGTTTCAGCCTAAAAACTCAAAATCTCTTCTTCTAAGAGCACAC
TGTCAGACATCGGATGGTCACTTACTGAGCAGGATCCCTACAATAATATTGTCCGTACTGCAATAGAAG
CAATGGCAGCAGTATTTGGAGGGACTCAGTCTTTGCACACAAATTCTTTTGATGAAGCTTTGGGTTTGCC
AACTGTGAAAAGTGCTCGAATTGCCAGGAACACACAAATCATCATTCAAGAAGAATCTGGGATTCCCAAA
GTGGCTGATCCTTGGGGAGGTTCTTACATGATGGAATGTCTCACAAATGATGTTTATGATGCTGCTTTAA
AGCTCATTAATGAAATTGAAGAAATGGGTGGAATGGCCAAAGCTGTAGCTGAGGGAATACCTAAACTTCG
AATTGAAGAATGTGCTGCCCGAAGACAAGCTAGAATAGATTCTGGTTCTGAAGTAATTGTTGGAGTAAAT
AAGTACCAGTTGGAAAAAGAAGACGCTGTAGAAGTTCTGGCAATTGATAATACTTCAGTGCGAAACAGGC
AGATTGAAAAACTTAAGAAGATCAAATCCAGCAGGGATCAAGCTTTGGCTGAACGTTGTCTTGCTGCACT
AACCGAATGTGCTGCTAGCGGAGATGGAAATATCCTGGCTCTTGCAGTGGATGCATCTCGGGCAAGATGT
ACAGTGGGAGAAATCACAGATGCCCTGAAAAAGGTATTTGGTGAACATAAAGCGAATGATCGAATGGTGA
GTGGAGCATATCGCCAGGAATTTGGAGAAAGTAAAGAGATAACATCTGCTATCAAGAGGGTTCATAAATT
CATGGAACGTGAAGGTCGCAGACCTCGTCTTCTTGTAGCAAAAATGGGACAAGATGGCCATGACAGAGGA
CCAAAAGTTATTGCTACAGGATTTGCTGATCTTGGTTTTGATGTGGACATAGGCCCTCTTTTCCAGACTC
CTCGTGAAGTGGCCCAGCAGGCTGTGGATGCGGATGTGCATGCTGTGGGCATAAGCACCCTCGCTGCTGG
TCATAAAACCCTAGTTCCTGAACTCATCAAAGAACTTAACTCCCTTGGACGGCCAGATATTCTTGTCATG
TGTGGAGGGGTGATACCACCTCAGGATTATGAATTTCTGTTTGAAGTTGGTGTTTCCAATGTATTTGGTC
CTGGGACTCGAATTCCAAAGGCTGCCGTTCAGGTGCTTGATGATATTGAGAAGTGTTTGGAAAAGAAGCA
GCAATCTGTATAA
```

Figure 4

```
Query: synMUT
Subject: MUT (NCBI Reference Sequence: NM_000255.3)

Alignment statistics for match #1
Score              Expect      Identities         Gaps              Strand
1665 bits(1846)    0.0         1721/2253(76%)     0/2253(0%)        Plus/Plus Query    1    ATGCTGAGAGCCAAAAACCACCTGTTCCTGCTGAGCCCCCACTATCTGAGACACGTCAAA    60
              ||| | ||||| || || ||||| ||  | ||     || || || ||||| ||||| |||
Sbjct    1    ATGTTAAGAGCTAAGAATCAGCTTTTTTACTTTCACCTCATTACCTGAGGCAGGTAAAA    60

Query    61   GAAAGTTCCGGGAGTAGACTGATCCAGCAGAGACTGCTGCACCAGCAGCAGCCACTGCAT   120
              |||    || ||    || || ||||| ||||  || ||||||||||  ||||| || ||
Sbjct    61   GAATCATCAGGCTCCAGGCTCATACAGCAACGACTTCTACACCAGCAACAGCCCCTTCAC   120

Query    121  CCTGAGTGGGCCGCTCTGGCCAAGAAACAGCTGAAGGGCAAAAACCCAGAAGACCTGATC   180
              || || ||||| || |||||| ||||  ||||||||||||||||||||||||||||  ||
Sbjct    121  CCAGAATGGGCTGCCCTGGCTAAAAAGCAGCTGAAAGGCAAAAACCCAGAAGACCTAATA   180

Query    181  TGGCACACTCCAGAGGGGATTTCAATCAAGCCCCTGTACAGCAAAAGGGACACTATGGAT   240
              |||||||| || || |||||  || || || ||| ||||   ||| || || |||||| |
Sbjct    181  TGGCACACCCCGGAAGGGATCTCTATAAAACCCTTGTATTCCAAGAGAGATACTATGGAC   240

Query    241  CTGCCAGAGGAACTGCCAGGAGTGAAGCCTTTCACCCGCGGACCTTACCCAACTATGTAT   300
              | || ||||| ||||| |||||||||||| |||||||| || ||||||| || ||||||
Sbjct    241  TTACCTGAAGAACTTCCAGGAGTGAAGCCATTCACACGTGGACCATATCCTACCATGTAT   300

Query    301  ACCTTTCGACCCTGGACAATTCGGCAGTACGCCGGCTTCACTACTGTGGAGGAATCAAAC   360
              ||||||  | |||||||||| || ||  ||||| ||||| || || || ||||| ||  |
Sbjct    301  ACCTTTAGGCCCTGGACCATCCGCCAGTATGCTGGTTTAGTACTGTGGAAGAAAGCAAT   360

Query    361  AAGTTTTATAAGGACAACATCAAGGCTGGACAGCAGGGCCTGAGTGTGGCATTCGATCTG   420
              ||||| |||||||||||||| ||||||| |||||| |   || || || || |||||||
Sbjct    361  AAGTTCTATAAGGACAACATTAAGGCTGGTCAGCAGGGATTATCAGTTGCCTTTGATCTG   420

Query    421  GCCACACATCGCGGCTATGACTCAGATAATCCCAGAGTCAGGGGGACGTGGGAATGGCA   480
              ||  ||||||| ||||||||| ||||| ||| ||  || | || || || ||||||||
Sbjct    421  GCGACACATCGTGGCTATGATTCAGACAACCCTCGAGTTCGTGGTGATGTTGGAATGGCT   480

Query    481  CGACTCGCTATCGACACAGTGGAAGATACTAAGATTCGTTCGATGGAATCCCTCTGGAG   540
              ||||| |||||  || ||||| ||||| || ||| || ||| |||||| |||| | ||
Sbjct    481  GGAGTTGCTATTGACACTGTGGAAGATACCAAAATTCTTTTTGATGGAATTCCTTTAGAA   540

Query    541  AAAATGTCTGTGAGTATGACAATGAACGGCGCTGTCATTCCCGTGCTGGCAAACTTCATC   600
              ||||||||| ||     || || || || || |||| || ||| || || ||||  |||
Sbjct    541  AAAATGTCAGTTTCCATGACTATGAATGGAGCAGTTATTCCAGTTCTTGCAAATTTTATA   600

Query    601  GTCACTGGCGAGGAACAGGGGGTGCCTAAGGAAAAACTGACGGCACAATTCAGAACGAC   660
              || |||||  ||||||| ||||| ||||| || || || |||| |||||| || ||||
Sbjct    601  GTAACTGGAGAAGAACAAGGTGTACCTAAAGAGAAGCTTACTGGTACCATCCAAAATGAT   660

Query    661  ATCCTGAAGCAGTTCATGGTGCCGAATACTTACATTTTTCCCCCTGAACCATCCATGAAA   720
              || || ||||| || ||||| ||  ||  || ||||||  || ||||| |||| |||||
Sbjct    661  ATACTAAAGGAATTTATGGTTCGAAATACATACATTTTTCCTCCAGAACCATCCATGAAA   720

Query    721  ATCATTGCCGATATCTTCGAGTACACCGCTAAGCACATGCCCAAGTTCAACTCAATTAGC   780
              || |||||||| ||| ||||||| ||  | ||||||||||||| | ||||| ||||| |
Sbjct    721  ATTATTGCTGACATATTTGAATATACAGCAAAGCACATGCCAAAATTTAATTCAATTTCA   780
```

Figure 4 (continued)

```
Query   781   ATCTCCGGGTATCATATGCAGGAAGCAGGAGCCGACGCTATTCTGGAGCTGGCTTACACC   840
              ||    ||    ||  || || ||  |||||||||||||||| || || |||||| || ||
Sbjct   781   ATTAGTGGATACCATATGCAGGAAGCAGGGGCTGATGCCATTCTGGAGCTGGCCTATACT   840

Query   841   CTGGCAGATGGCCTGGAATATTCTCGAACCGGACTGCAGGCAGGCCTGACAATCGACGAG   900
              | ||||||||    |||| || ||| |||| ||||| ||||| |||||||||| || ||
Sbjct   841   TTAGCAGATGGATTGGAGTACTCTAGAACTGGACTCCAGGCTGGCCTGACAATTGATGAA   900

Query   901   TTCGCTCCTAGACTGAGTTTCTTTTGGGGAATTGGCATGAACTTTTACATGGAGATCGCC   960
              || || || ||   || |||||| |||||||||| ||||| || ||||||| || ||
Sbjct   901   TTTGCACCAAGCTTGTCTTTCTTCTGGGCAATTGGAATGAATTTCTATATGGAAATAGCA   960

Query   961   AAGATGAGGGCTGGCCGGAGACTGTGGGCACACCTGATCGAGAAGATGTTCCAGCCTAAG   1020
              ||||||||   |||    || ||| ||||| ||  |||||| |||| || |||||||||
Sbjct   961   AAGATGAGAGCTGGTAGAAGACTCTGGGCTCACTTAATAGAGAAAATGTTTCAGCCTAAA   1020

Query   1021  AACTCTAAGAGTCTCCTGCTGCGGCCCCATTGCCAGACATCCGGCTGGTCTCTCACTGAA   1080
              |||||  || ||| ||  |   ||  | ||    ||||||| || || |||| || |||
Sbjct   1021  AACTCAAAATCTCTTCTTCTAAGAGCACACTGTCAGACATCTGGATGGTCACTTACTGAG   1080

Query   1081  CAGGACCCATATAACAATATTGTCAGAACCGCAATCGAGGCAATGGCAGCCGTGTTCGGA   1140
              ||||| || ||  || |||||| ||  ||| ||||| || ||||| ||||| ||| |||
Sbjct   1081  CAGGATCCCTACAATAATATTGTCCGTACCGCAATAGAAGCAATGGCAGCAGTATTTGGA   1140

Query   1141  GGAACCCAGAGCCTGCACACAAACTCCTTTGATGAGGCCCTGGGGCTGCCTACCGTGAAG   1200
              |  || ||   ||   ||||||| ||||||||||   || |||| ||||| || |||||
Sbjct   1141  GGGACTCAGTCTTTGCACACAAATTCTTTTGATGAAGCTTTGGGTTTGCCAACTGTGAAA   1200

Query   1201  TCTGCTACGATTGCACGCAATACACAGATCATTATCCAGGAGGAATCCGGAATCCCAAAG   1260
              |  | | ||||| |  || |||||||||||||||| |||||| ||||| || || ||||
Sbjct   1201  AGTGCTCGAATTGCCAGGAACACACAAATCATCATTCAAGAAGAATCTGGGATTCCCAAA   1260

Query   1261  GTGGCCGATCCCTGGGGAGGCTCTTACATGATGGAGTGCCTGACAAACGACGTGTATGAT   1320
              |||| | ||||| ||||||| ||||||||||||| ||| || ||  | || || |||||
Sbjct   1261  GTGGCTGATCCTTGGGGAGGTTCTTACATGATGGAATGTCTCACAAATGATGTTTATGAT   1320

Query   1321  GCTGCACTGAAGCTGATTAATGAAATCGAGGAAATGGGGGGAATGGCAAAGGCCGTGGCT   1380
              |||| |  || |||| |||||||| || ||||| ||||| || ||||||||| || |||
Sbjct   1321  GCTGCTTTAAAGCTCATTAATGAAATTGAAGAAATGGGTGGAATGGCCAAAGCTGTAGCT   1380

Query   1381  GACGGCATTCCAAAACTGACGATCGAGGAATCTGCAGCTAGCGCCCAGGCACGAATTGAC   1440
              |  || || || |||| |  || || || |||    || || |||| || || || |||
Sbjct   1381  GAGGGAATACCTAAACTTGAATTGAAGAATGTGCTGCCCGAAGACAAGCTAGAATAGAT   1440

Query   1441  TCAGGAAGCGAAGTGATCGTCGGGGTGAATAAGTACCAGCTGGAGAAAGAAGACGCAGTC   1500
              || ||     ||||  ||||| || ||||||||||||||||||||||||||||| || |
Sbjct   1441  TCTGGTTCTGAACTAATTGTTGGACTAAATAAGTACCAGTTGGAAAAAGAAGACGCTGTA   1500

Query   1501  GAAGTGCTGGCCATCGATAACACAAGCGTGCGCAATCGACAGATTGAGAAGCTGAAGAAA   1560
              ||||| ||||| || ||||||||| |  |||| | |||||||||||  |||| |||||
Sbjct   1501  GAAGTTCTGGCAATTGATAATACTTCAGTGCGAAACAGGCAGATTGAAAAACTTAAGAAG   1560

Query   1561  ATCAAAAGCTCCCGCGATCAGGCACTGGCCGAACGATGCCTGGCAGCCCTGACTGAGTGT   1620
              ||||||   |  |  | |||||||| || |||| ||| ||   ||||| || || ||||
Sbjct   1561  ATCAAATCCAGCAGGGATCAAGCTTTGGCTGAACGTTGTCTTGCTGCACTAACCGAATGT   1620

Query   1621  GCTGCAAGCGGGGACGGAAACATTCTGGCTCTGGCAGTCGATGCCTCCGGGCTAGATGC   1680
              |||| ||||| |||||| ||||  |||||||  |||||||||| ||||  ||| ||||
Sbjct   1621  GCTGCTAGCGGAGATGGAAATATCCTGGCTCTTGCAGTGGATGCATCTCGGGCAAGATGT   1680
```

Figure 4 (continued)

```
Query  1681  ACTGTGGGGGAAATCACCGACGCCCTGAAGAAAGTCTTCGGAGAGCACAAGGCCAATGAT  1740
             ||  ||||| ||||||||| ||  |||||||| ||  ||  ||  || || ||  ||||||
Sbjct  1681  ACAGTGGGAGAAATCACAGATGCCCTGAAAAAGGTATTCGTGAACATAAAGCGAATGAT  1740

Query  1741  CGGATGGTGAGCGGCGCTTATAGACAGGAGTTCGGGGAATCTAAACAGATTACCAGTGCC  1800
             || ||||||||||  || || |||  | ||||| ||  ||  |||||||| ||   |||
Sbjct  1741  CGAATGGTGAGTGGAGCATATCGCCAGGAATTTGGAGAAAGTAAAGAGATAACATCTGCT  1800

Query  1801  ATCAAGAGGCTGCACAAGTTCATGGACACAGAAGGGCGACGCCCAGGCTGCTGGTCGCA  1860
             ||||||||| ||  |  || |||||||| |||||| | ||| | ||| || ||| |||
Sbjct  1801  ATCAAGAGGGTTCATAAATTCATGGAACGTGAAGGTCGCAGACCTCGTCTTCTTGTAGCA  1860

Query  1861  AAGATGGGACAGGACGGACATGATCGCGGAGCAAAAGTCATTGCCACCGGGTTCGCTGAC  1920
             ||  ||||||| || |||  || || | ||||||||||| |||| ||| ||| ||||
Sbjct  1861  AAAATGGGACAAGATGGCCATGACAGAGGAGCAAAAGTTATTGCTACAGGATTTGCTGAT  1920

Query  1921  CTGGGATTTGACGTGGATATCGGCCCTCTGTTCCAGACACCACGAGAGGTCGCACAGCAG  1980
             || ||  ||||| ||||| |  ||||||| ||||||||  ||  || ||| || ||||
Sbjct  1921  CTTGGTTTTGATGTGGACATAGGCCCTCTTTTCCAGACTCCTCGTGAAGTGGCCCAGCAG  1980

Query  1981  GCAGTCGACGCTGATGTGCACGCAGTCGGAGTGTCCACTCTGGCAGCTGGCCATAAGACC  2040
             || || || || ||||| || ||  | |||   || || | || || |||  ||| |||
Sbjct  1981  GCTGTGGATGCGGATGTGCATGCTGTGGGCATAAGCACCCTGGCTGCTGGTCATAAAACC  2040

Query  2041  CTGGTGCCTCAACTGATCAAAGAGCTGAACTCTCTGGGCAGACCAGACATCCTGGTCATG  2100
             ||  || ||  ||| ||||||||||| |||| |||| | ||  ||||||  |||| |||
Sbjct  2041  CTAGTTCCTGAACTCATCAAAGAACTTAACTCCCTTGGACGGCCAGATATTCTTGTCATG  2100

Query  2101  TGCGGCGGCGTGATCCCACCCCAGGATTACGAATTCCTGTTTGAGGTCGGGGTGAGCAAC  2160
             || ||  || | || ||||| |||||| |  |||||| ||||||  ||  ||  |||
Sbjct  2101  TGTGGAGGGTGATACCACCTCAGGATTATGAATTTCTGTTTGAAGTTGGTGTTCCAAT  2160

Query  2161  GTGTTCGGACCAGGAACCAGGATCCCTAAGGCCGCAGTGCAGGTCCTGGATGATATTGAA  2220
             || ||  ||  ||  |   |||| || | ||  || ||||| ||  || |||||||| |
Sbjct  2161  GTATTTGGTCCTGGACTCGAATTCCAAAGGCTGCCGTTCAGGTGCTTGATGATATTGAG  2220

Query  2221  AAGTGTCTGGAAAAGAAACAGCAGTCAGTGTAA      2253
             ||||| || ||||||||  ||||  |||| |||
Sbjct  2221  AAGTGTTTGGAAAAGAAGCAGCAATCTGTATAA      2253
```

Figure 5

```
ATG CTG AGA GCC AAA AAC CAG CTG TTC CTG CTG AGC CCC CAC
 M   L   R   A   K   N   Q   L   F   L   L   S   P   H

TAT CTG AGA CAG GTC AAA GAA AGT TCC GGG AGT AGA CTG ATC
              1
 Y   L   R   Q   V   K   E   S   S   G   S   R   L   I

CAG CAG AGA CTG CTG CAC CAG CAG CAG CCA CTG CAT CCT GAG
 Q   Q   R   L   L   H   Q   Q   Q   P   L   H   P   E

TGG GCC GCT CTG GCC AAG AAA CAG CTG AAG GGC AAA AAC CCA
                              1
 W   A   A   L   A   K   K   Q   L   K   G   K   N   P

GAA GAC CTG ATC TGG CAC ACT CCA GAG GGG ATT TCA ATC AAG
                                                 1
 E   D   L   I   W   H   T   P   E   G   I   S   I   K

CCC CTG TAC AGC AAA AGG GAC ACT ATG GAT CTG CCA GAG GAA
                                          1
 P   L   Y   S   K   R   D   T   M   D   L   P   E   E

CTG CCA GGA GTG AAG CCT TTC ACC CGC GGA CCT TAC CCA ACT
                                          2
                                          1
 L   P   G   V   K   P   F   T   R   G   P   Y   P   T

ATG TAT ACC TTT CGA CCC TGG ACA ATT CGG CAG TAC GCC GGC
                                              1
 M   Y   T   F   R   P   W   T   I   R   Q   Y   A   G

TTC AGT ACT GTG GAG GAA TCA AAC AAG TTT TAT AAG GAC AAC
                                      1
 F   S   T   V   E   E   S   N   K   F   Y   K   D   N

ATC AAG GCT GGA CAG CAG GGC CTG AGT GTG GCA TTC GAT CTG
                  1
 I   K   A   G   Q   Q   G   L   S   V   A   F   D   L

GCC ACA CAT CGC GGC TAT GAC TCA GAT AAT CCC AGA GTC AGG
 A   T   H   R   G   Y   D   S   D   N   P   R   V   R

GGG GAC GTG GGA ATG GCA GGA GTC GCT ATC GAC ACA GTG GAA
 G   D   V   G   M   A   G   V   A   I   D   T   V   E

GAT ACT AAG ATT CTG TTC GAT GGA ATC CCT CTG GAG AAA ATG
 D   T   K   I   L   F   D   G   I   P   L   E   K   M
```

Figure 5 (continued)

| TCT | GTG | AGT | ATG | ACA | ATG | AAC | GGC | GCT | GTC | ATT | CCC | GTG | CTG |
|---|---|---|---|---|---|---|---|---|---|---|---|---|---|
|   |   |   | 1 |   |   | 1 |   |   |   |   |   |   |   |
| S | V | S | M | T | M | N | G | A | V | I | P | V | L |

| GCA | AAC | TTC | ATC | GTC | ACT | GGC | GAG | GAA | CAG | GGG | GTG | CCT | AAG |
|---|---|---|---|---|---|---|---|---|---|---|---|---|---|
|   |   |   |   |   |   |   |   |   |   | 1 |   |   |   |
| A | N | F | I | V | T | G | E | E | Q | G | V | P | K |

| GAA | AAA | CTG | ACC | GGC | ACA | ATT | CAG | AAC | GAC | ATC | CTG | AAG | GAG |
|---|---|---|---|---|---|---|---|---|---|---|---|---|---|
|   | 1 |   |   |   |   |   |   |   |   |   |   |   |   |
| E | K | L | T | G | T | I | Q | N | D | I | L | K | E |

| TTC | ATG | GTG | CGG | AAT | ACT | TAC | ATT | TTT | CCC | CCT | GAA | CCA | TCC |
|---|---|---|---|---|---|---|---|---|---|---|---|---|---|
|   |   |   |   |   |   |   |   |   |   |   |   | 1 |   |
| F | M | V | R | N | T | Y | I | F | P | P | E | P | S |

| ATG | AAA | ATC | ATT | GCC | GAT | ATC | TTC | GAG | TAC | ACC | GCT | AAG | CAC |
|---|---|---|---|---|---|---|---|---|---|---|---|---|---|
|   |   | 1 |   |   |   |   |   |   |   |   |   |   | 1 |
| M | K | I | I | A | D | I | F | E | Y | T | A | K | H |

| ATG | CCC | AAG | TTC | AAC | TCA | ATT | AGC | ATC | TCC | GGG | TAT | CAT | ATG |
|---|---|---|---|---|---|---|---|---|---|---|---|---|---|
|   |   |   |   |   |   |   |   | 1 |   |   |   |   |   |
| M | P | K | F | N | S | I | S | I | S | G | Y | H | M |

| CAG | GAA | GCA | GGA | GCC | GAC | GCT | ATT | CTG | GAG | CTG | GCT | TAC | ACC |
|---|---|---|---|---|---|---|---|---|---|---|---|---|---|
|   |   |   |   |   |   |   |   |   |   |   |   | 1 |   |
| Q | E | A | G | A | D | A | I | L | E | L | A | Y | T |

| CTG | GCA | GAT | GGC | CTG | GAA | TAT | TCT | CGA | ACC | GGA | CTG | CAG | GCA |
|---|---|---|---|---|---|---|---|---|---|---|---|---|---|
|   |   |   |   |   |   |   |   |   |   |   |   | 1 |   |
| L | A | D | G | L | E | Y | S | R | T | G | L | Q | A |

| GGC | CTG | ACA | ATC | GAC | GAG | TTC | GCT | CCT | AGA | CTG | AGT | TTC | TTT |
|---|---|---|---|---|---|---|---|---|---|---|---|---|---|
| G | L | T | I | D | E | F | A | P | R | L | S | F | F |

| TGG | GGA | ATT | GGC | ATG | AAC | TTT | TAC | ATG | GAG | ATC | GCC | AAG | ATG |
|---|---|---|---|---|---|---|---|---|---|---|---|---|---|
| W | G | I | G | M | N | F | Y | M | E | I | A | K | M |

| AGG | GCT | GGC | CGG | AGA | CTG | TGG | GCA | CAC | CTG | ATC | GAG | AAG | ATG |
|---|---|---|---|---|---|---|---|---|---|---|---|---|---|
|   |   |   |   |   |   |   |   |   |   |   |   |   | 1 |
| R | A | G | R | R | L | W | A | H | L | I | E | K | M |

| TTC | CAG | CCT | AAG | AAC | TCT | AAG | AGT | CTG | CTG | CTG | CGG | GCC | CAT |
|---|---|---|---|---|---|---|---|---|---|---|---|---|---|
|   |   |   |   |   |   |   |   | 1 |   |   |   |   |   |
| F | Q | P | K | N | S | K | S | L | L | L | R | A | H |

| TGC | CAG | ACA | TCC | GGC | TGG | TCT | CTG | ACT | GAA | CAG | GAC | CCA | TAT |
|---|---|---|---|---|---|---|---|---|---|---|---|---|---|
| C | Q | T | S | G | W | S | L | T | E | Q | D | P | Y |

Figure 5 (continued)

| AAC | AAT | ATT | GTC | AGA | ACC | GCA | ATC | GAG | GCA | ATG | GCA | GCC | GTG |
|-----|-----|-----|-----|-----|-----|-----|-----|-----|-----|-----|-----|-----|-----|
|     |     |     |     |     | 1   |     | 1   |     |     | 1   |     |     |     |
| N   | N   | I   | V   | R   | T   | A   | I   | E   | A   | M   | A   | A   | V   |

| TTC | GGA | GGA | ACC | CAG | AGC | CTG | CAC | ACA | AAC | TCC | TTT | GAT | GAG |
|-----|-----|-----|-----|-----|-----|-----|-----|-----|-----|-----|-----|-----|-----|
| F   | G   | G   | T   | Q   | S   | L   | H   | T   | N   | S   | F   | D   | E   |

| GCC | CTG | GGG | CTG | CCT | ACC | GTG | AAG | TCT | GCT | AGG | ATT | GCA | CGC |
|-----|-----|-----|-----|-----|-----|-----|-----|-----|-----|-----|-----|-----|-----|
|     |     |     |     |     |     |     |     |     | 1   |     |     |     |     |
| A   | L   | G   | L   | P   | T   | V   | K   | S   | A   | R   | I   | A   | R   |

| AAT | ACA | CAG | ATC | ATT | ATC | CAG | GAG | GAA | TCC | GGA | ATC | CCA | AAG |
|-----|-----|-----|-----|-----|-----|-----|-----|-----|-----|-----|-----|-----|-----|
| N   | T   | Q   | I   | I   | I   | Q   | E   | E   | S   | G   | I   | P   | K   |

| GTG | GCC | GAT | CCC | TGG | GGA | GGC | TCT | TAC | ATG | ATG | GAG | TGC | CTG |
|-----|-----|-----|-----|-----|-----|-----|-----|-----|-----|-----|-----|-----|-----|
|     |     |     | 1   |     |     |     |     |     |     |     |     | 1   |     |
| V   | A   | D   | P   | W   | G   | G   | S   | Y   | M   | M   | E   | C   | L   |

| ACA | AAC | GAC | GTG | TAT | GAT | GCT | GCA | CTG | AAG | CTG | ATT | AAT | GAA |
|-----|-----|-----|-----|-----|-----|-----|-----|-----|-----|-----|-----|-----|-----|
| 1   |     |     |     |     |     |     |     |     |     |     |     |     |     |
| T   | N   | D   | V   | Y   | D   | A   | A   | L   | K   | L   | I   | N   | E   |

| ATC | GAG | GAA | ATG | GGG | GGA | ATG | GCA | AAG | GCC | GTG | GCT | GAG | GGC |
|-----|-----|-----|-----|-----|-----|-----|-----|-----|-----|-----|-----|-----|-----|
| I   | E   | E   | M   | G   | G   | M   | A   | K   | A   | V   | A   | E   | G   |

| ATT | CCA | AAA | CTG | AGG | ATC | GAG | GAA | TGT | GCA | GCT | AGG | CGC | CAG |
|-----|-----|-----|-----|-----|-----|-----|-----|-----|-----|-----|-----|-----|-----|
|     |     |     |     | 1   | 1   |     |     |     |     | 1   | 1   |     |     |
| I   | P   | K   | L   | R   | I   | E   | E   | C   | A   | A   | R   | R   | Q   |

| GCA | CGA | ATT | GAC | TCA | GGA | AGC | GAA | GTG | ATC | GTC | GGG | GTG | AAT |
|-----|-----|-----|-----|-----|-----|-----|-----|-----|-----|-----|-----|-----|-----|
| A   | R   | I   | D   | S   | G   | S   | E   | V   | I   | V   | G   | V   | N   |

| AAG | TAC | CAG | CTG | GAG | AAA | GAA | GAC | GCA | GTC | GAA | GTG | CTG | GCC |
|-----|-----|-----|-----|-----|-----|-----|-----|-----|-----|-----|-----|-----|-----|
|     |     |     |     |     |     |     | 1   | 1   |     |     |     |     | 1   |
| K   | Y   | Q   | L   | E   | K   | E   | D   | A   | V   | E   | V   | L   | A   |

| ATC | GAT | AAC | ACA | AGC | GTG | CGC | AAT | CGA | CAG | ATT | GAG | AAG | CTG |
|-----|-----|-----|-----|-----|-----|-----|-----|-----|-----|-----|-----|-----|-----|
| I   | D   | N   | T   | S   | V   | R   | N   | R   | Q   | I   | E   | K   | L   |

| AAG | AAA | ATC | AAA | AGC | TCC | CGC | GAT | CAG | GCA | CTG | GCC | GAA | CGA |
|-----|-----|-----|-----|-----|-----|-----|-----|-----|-----|-----|-----|-----|-----|
|     | 1   |     | 1   |     | 2   |     |     |     |     |     |     |     | 1   |
| K   | K   | I   | K   | S   | S   | R   | D   | Q   | A   | L   | A   | E   | R   |

| TGC | CTG | GCA | GCC | CTG | ACT | GAG | TGT | GCT | GCA | AGC | GGG | GAC | GGA |
|-----|-----|-----|-----|-----|-----|-----|-----|-----|-----|-----|-----|-----|-----|
| 1   |     |     | 1   |     |     |     |     |     |     | 1   | 1   |     |     |
| C   | L   | A   | A   | L   | T   | E   | C   | A   | A   | S   | G   | D   | G   |

Figure 5 (continued)

| AAC | ATT | CTG | GCT | CTG | GCA | GTC | GAT | GCC | TCC | CGG | GCT | AGA | TGC |
|-----|-----|-----|-----|-----|-----|-----|-----|-----|-----|-----|-----|-----|-----|
| N | I | L | A | L | A | V | D | A | S | R | A | R | C |

| ACT | GTG | GGG | GAA | ATC | ACC | GAC | GCC | CTG | AAG | AAA | GTC | TTC | GGA |
| T | V | G | E | I | T | D | A | L | K | K | V | F | G |

| GAG | CAC | AAG | GCC | AAT | GAT | CGG | ATG | GTG | AGC | GGC | GCT | TAT | AGA |
|     |     |     | 2   |     |     |     |     |     |     |     |     |     | 1   |
|     |     |     |     |     |     |     |     |     |     |     |     |     | 2   |
| E | H | K | A | N | D | R | M | V | S | G | A | Y | R |

| CAG | GAG | TTC | GGG | GAA | TCT | AAA | GAG | ATT | ACC | AGT | GCC | ATC | AAG |
|     |     |     |     | 2   |     |     |     | 1   |     |     |     |     |     |
| Q | E | F | G | E | S | K | E | I | T | S | A | I | K |

| AGG | GTG | CAC | AAG | TTC | ATG | GAG | AGA | GAA | GGG | CGA | CGG | CCC | AGG |
|     |     |     |     |     |     |     |     |     |     | 1   |     |     |     |
| R | V | H | K | F | M | E | R | E | G | R | R | P | R |

| CTG | CTG | GTG | GCA | AAG | ATG | GGA | CAG | GAC | GGA | CAT | GAT | CGC | GGA |
|     |     |     |     |     |     | 1   |     |     |     | 1   |     |     | 1   |
| L | L | V | A | K | M | G | Q | D | G | H | D | R | G |

| GCA | AAA | GTC | ATT | GCC | ACC | GGG | TTC | GCT | GAC | CTG | GGA | TTT | GAC |
| A | K | V | I | A | T | G | F | A | D | L | G | F | D |

| GTG | GAT | ATC | GGC | CCT | CTG | TTC | CAG | ACA | CCA | CGA | GAG | GTC | GCA |
|     |     |     |     |     |     |     |     | 2   |     |     |     | 1   |     |
| V | D | I | G | P | L | F | Q | T | P | R | E | V | A |

| CAG | CAG | GCA | GTC | GAC | GCT | GAT | GTG | CAC | GCA | GTC | GGA | GTG | TCC |
|     |     |     |     |     | 2   |     |     |     |     |     |     | 1   |     |
|     |     |     |     |     | 1   |     |     |     |     |     |     |     |     |
| Q | Q | A | V | D | A | D | V | H | A | V | G | V | S |

| ACT | CTG | GCA | GCT | GGC | CAT | AAG | ACC | CTG | GTG | CCT | GAA | CTG | ATC |
|     |     | 2   |     |     |     |     |     |     |     |     |     |     |     |
|     |     | 1   | 1   |     | 1   |     |     |     |     |     |     |     |     |
| T | L | A | A | G | H | K | T | L | V | P | E | L | I |

| AAA | GAG | CTG | AAC | TCT | CTG | GGC | AGA | CCA | GAC | ATC | CTG | GTC | ATG |
|     |     |     |     |     |     |     |     |     |     |     |     |     | 1   |
| K | E | L | N | S | L | G | R | P | D | I | L | V | M |

| TGC | GGC | GGC | GTG | ATC | CCA | CCC | CAG | GAT | TAC | GAA | TTC | CTG | TTT |
|     | 1   |     |     |     |     |     |     |     |     |     |     |     |     |
| C | G | G | V | I | P | P | Q | D | Y | E | F | L | F |

| GAG | GTC | GGG | GTG | AGC | AAC | GTG | TTC | GGA | CCA | GGA | ACC | AGG | ATC |
| E | V | G | V | S | N | V | F | G | P | G | T | R | I |

Figure 5 (continued)

```
CCT  AAG  GCC  GCA  GTG  CAG  GTC  CTG  GAT  GAT  ATT  GAA  AAG  TGT
              2                                           1
 P    K    A    A    V    Q    V    L    D    D    I    E    K    C

CTG  GAA  AAG  AAA  CAG  CAG  TCA  GTG  TAA
 L    E    K    K    Q    Q    S    V
```

Adeno-associated Virus *syn*MUT Expression Cassette

ITR=adeno-associated virus inverted terminal repeats
HCR=hepatic control region
hAAT= human alpha-anti-trypsin promoter (liver specific expression)
*syn*MUT= synthetic human methylmalonyl-CoA synthetase
Poly-A=polyadenylation signal

Figure 12

| Allele | | Percent Identity to hMUT |
|---|---|---|
| hMUT | SEQ ID NO:3 | 100 |
| synMUT1 | SEQ ID NO:1 | 76.4 |
| synMUT2 | SEQ ID NO:4 | 76.0 |
| synMUT3 | SEQ ID NO:5 | 76.2 |
| synMUT4 | SEQ ID NO:6 | 75.7 |

Figure 13

| Allele | | Percent Identity to synMUT1 |
|---|---|---|
| hMUT | SEQ ID NO:3 | 76.4 |
| synMUT1 | SEQ ID NO:1 | 100 |
| synMUT2 | SEQ ID NO:4 | 79.0 |
| synMUT3 | SEQ ID NO:5 | 78.7 |
| synMUT4 | SEQ ID NO:6 | 80.8 |

Figure 15

```
SEQ ID NO:3  hMUT     ATGTTAAGAGCTAAGAATCAGCTTTTTTTACTTTCACCTCATTACCTGAG  50
SEQ ID NO:1  synMUT1  ATGCTGAGAGCCAAAAACCAGCTGTTCCTGCTGAGCCCCACTATCTGAG
SEQ ID NO:4  synMUT2  ATGCTGCGAGCGAAAAATCAGCTTTTTCTGTTGAGCCCACACTACCTGAG
SEQ ID NO:5  synMUT3  ATGTTGAGGGCTAAAAACCAGCTCTTTCTGTTGAGTCCACACTACCTTAG
SEQ ID NO:6  synMUT4  ATGCTTCCGCCAAGAACCAACTGTTCCTGCTCTCCCCCCACTACCTCCS
                     ***  *   *   **  *    *   *    *  * hMUT     GCAGGTAAAAGAATCATCAGGCTCCAGGCTCATACAGCAACGACTTCTAC
             synMUT1  ACGGGTCAAGGAAGTTCGGGGAGTAGACTGATCCAGCAGGAACTGCTGC
             synMUT2  GCAGGTAAAAGAATCCAGCGGGAGCCGGCTGATCCAGCAGCGACTGCTGC
             synMUT3  GCAGGTGAAGGAATCTAGCGGTAGCAGGCTGATCCAGCAGCGCCTGCTGC
             synMUT4  ACAAGTCAAGGAGAGCTCCGGAAGCCGCCTGATTCAGCAGCGGCTGCTGC
                                       * hMUT     ACCAGCAACAGCCCCTTCACCCAGAATGGCTGCCTTGGCTAAAAAGCAG
             synMUT1  ACCAGCAGCAGCCACTGCATCCTGAGTGGGCCGCTCTGGCCAACAAACAG
             synMUT2  ACCAGCAGCAGCCTTTGCATCCGGAATGGGCTGCTTTGGCGAAGAAGCAG
             synMUT3  ACCAGCAGCAGCCCCTGCACCCTGAGTGAGCTGCATTGGCAAAGAAACAA
             synMUT4  ACCAGCAGCAGCCCCTGCATCCGGAATGGGCAGCGTTCGCAAAGAAGCAG
                      *****  *           ***      ** hMUT     CTGAAAGGCAAAATCCAGAAGCACCTAATATGCCACACCCGGAAGGGAT
             synMUT1  CTGAAAGGCAAAAATCCAGAAGGACCTGATCTGGCACACTCCAGAGGGAT
             synMUT2  CTCAAGGGGAAGAACCCTGAAGATCTTATTTGGCACACACCCAGAGGGCAT
             synMUT3  CTGAAGGGCTAAAAATCCTGAAGATCTGATTGGCACACACCGGAGGGCAT
             synMUT4  CTGAGGGGAAAGACCCCTGAGGACCTGATCGGCACACCCGGAGGGAAT
                              ****             * hMUT     CTCTATAAAACCCTTGTATTCCAAGAGAGATACTATGGACTTACCTGAAG
             synMUT1  TTCAATCAAGCCCTGTACAGCAAAGGGACACTATGGATCTGCCAGAGG
             synMUT2  CAGCATCAAGCCTTTGTATTCCAAAAGGGACACCATGGATCTGCCTGAAG
             synMUT3  TTCCATAAAACCTCTCTACTGTAAACGCCATACTATGGACTGCCCGAGG
             synMUT4  CTCGATCAAGCCACTGTACTCCAAAAGGGACACCATGGACTTGCCTGAAG
                                       *        ** hMUT     AACTTCCAGGAGTGAAGCCATTCACACGTGGACCCATATCCTACATGTAT
             synMUT1  AACTGCCAGGAGTGAAGCCTTTCACCCCGCGGACCTTACCCGCACTATGTAT
             synMUT2  AATTGCCTGGGGTCAAACCATTCACACGGGGGCCATATCCAACCATGTAC
             synMUT3  AATTGCCAGGAGTGAAACCCTTTACAAGGCGGGCCCTACCCACTATGTAC
             synMUT4  AACTTCCGGGCGGGAAGCCTTTTACCCGGGGGCCATACCCAACAATGTAC
                         ** *                 **  *  **** hMUT     ACCTTTAGCCCTGGACCATCCGCCAGTATGCTGGTTTTAGTACTGTGGA
             synMUT1  ACCTTTCGACCCTGGACAATTCGGCAGTACGCCGGCTTCAGTACTGTGGA
             synMUT2  ACCTTCCGGCCATGGACTATCAGACAGTATGCAGGCTTTAGCACTGTCGA
             synMUT3  AGGTTCAGACCCTACATACGCCGGATTTTCTACCGTTGA
             synMUT4  ACTTTCCGCCCCTGGACCATCAGACAGTACGCCGGTTTCTCCACCGTCGA
                      *  **   *    *    *  **       ** hMUT     AGAAGCAATAAGTTCTATAAGGACAACATTAAGGCTGGTCAGCAGGGAT
             synMUT1  GGAATCAAATAAGTTTTATAAGGACAATCAGGCTCGACAGCAGGCD
             synMUT2  GGAATCCAATAAGTTCTATAAAGACAATATCAAAGCTGGCCAGCAAGGTC
             synMUT3  GGAATCCAACAAGTTTTATAAGGACAACATCAAAGCCGGCAGCAGGGAC
             synMUT4  AGAATCCAACAAGTTCTATAAGGACAACATCAAGGCCGGCAGCAGGGAC
                              *       *   ** hMUT     TATCAGTTGCCTTTGATGTGGCGACACATCGTGGCTATGATTCAGACAAC
             synMUT1  TGTCAGTGGCCATTCGATCTGGCTACACATCGCGGCTATGACTCAGATAAT
             synMUT2  TGTCCGTGGCCATTCGATCTGGCTACACATACAGGTTATGATTCTGACAAT
             synMUT3  TGTCAGTGGCCATTTGATCTGGCCACACCGCGGGTACTACCTCCGACAAC
             synMUT4  TGAGGTCGGCGTTTGACCTGGCAACCCATCGCGGCTACGACTCGACAAC
                      *            **       *         ** hMUT     CCTCGAGTTGGTGGTGATGTTGGAATGCCTGGAGTTCCTATTGACACTGT
             synMUT1  CCGCAGAGTCGGGGCGATGTGGGAGACCTGGAGTTCCTCATCGACACAGT
             synMUT2  CCAGAGTAGGGGGGAGACCTGGAATGCGCGGAGTTCCCATTGACACAGT
             synMUT3  CCAAGAGTCCGCGGTGACCTCGGCATGGCAGGGGTTCCCATTGACACAGT
             synMUT4  CCTCGCGTGCGGGGGGACGTGGGAATGGCGCGAGTGGCTATCGACACCGT
                              *                ** hMUT     CGAAGATACCAAAATTCTTTTTGATGGAATTCCTTTAGAAAAAATGTCAG  500
             synMUT1  GGAAGATACTAAGATTCTGTTCGATGGAATCCCTCTGGAGAAAATGTCTG
```

```
syn80T2        TCCGGTGCAGTGATCCCCCGCAGGATTAGGAATTCCTCTTCCAAGTAGG
syn80T3        TGCGGTGGGGTAATCCCCCCCAAGACTACGAGTTCCTTTTCGAAGTGCG
syn80T4        TGTGGGGGAGTGATTCCCCCACAAGACTACGAGTTCCTGTTCGAAGTCGG
                           ****   ******  * hMUT           TGTTTCCAATGTATTTGGTCCTGGGACTCGAAGTCCAAAGGCTGCCGTTC
syn80T1        GGTGAGCAACGTGTTCGGACCAGGAACCAGGATCCCTAAGGCCGCAGTGC
syn80T2        AGTGTCAAACGTGTTCGGCCCAGGCACTCGATACCCAAGGCTGCCGTTC
syn80T3        TGTTTCTAACGTGTTCGGACCTGGAACAAGAATCCCTAAGGCGGCAGTCC
syn80T4        CGTGTCCAACGTGTTCGGTCCCGGAACCAGAATCCCGAAGGGTGCGGTCC
               *    *  ** * ** *     *     ***** *  * * hMUT           AGGTGCTTGATGATATTGAGAAGTGTTTGAAAAGAAGCAGCAATCTGTA 2250
syn80T1        AGGTCCTGGATGATATTGAAAAGTGTCTGGAAAAGAAACAGCAGTCAGTG
syn80T2        AGGTGCTTGACGGCATTGAAAAATGTCTGGAGAAGAAGCCACAATCTGTA
syn80T3        AGGTGCTTGACGATATCGAGAAGTGCCTGGAGAAAAAGCAACAATCCGTT
syn80T4        AAGTGCTGGATGATATTGAGAAGTGCCTTGAGAAAAAGCAACAGTCAGTG
               *    ** *       *     *  * hMUT           TAA
syn80T1        TAA
syn80T2        TAA
syn80T3        TAA
syn80T4        TGA
               *  *
```

Figure 16

| | | |
|---|---|---|
| SEQ ID NO:1 synMUT1 | ATGCTGGAGCCAAAAACCAGCTGTTCTGCTGAGCCCCACTATCTGAG | 50 |
| SEQ ID NO:4 synMUT2 | ATGCTGCGAGCCAAAAATCAGCTTTTCTGTTGAGCCCACACTACCTGAG | |
| SEQ ID NO:5 synMUT3 | ATGTTGAGGCTAAAAACCAGCTCTTTCTGTTGAGTCCACACTACCTTAG | |
| SEQ ID NO:6 synMUT4 | ATGCTTCGCCCAAGAACCAACTGTTCTGCTGTCCCCCACTACCTCCG | | synMUT1  ACAGGTCAAAGGAAGTTCTCGGAGTAGACTGATCCAGCAGAGACTGCTGC
synMUT2  GCAGGTTAAAGGATCCAGCGCGAGCCGGCTGATTCAGCAGCGACTGCTCC
synMUT3  GCAAGTGAAAGGAATGTAGCGGTAGCAGGCTGATCCAGCAGCGCCTGCTGG
synMUT4  ACAAGTCAAGCGAGCTCGCGAGCCGCCTGATTCAGCAGCGGCTGCTGC synMUT1  ACCAGCAGCAGCCACTGCATCCTGAGTGGGCCGCTCTGGCCAAGAAACAG
synMUT2  ACCAGCAGCAGCCTTTGCATCCCGAATGGGCTGCTTTGGCGAAGAAGCAG
synMUT3  ACCAGCAGCAGCCCCTGCACCCTGAGTGGGCTGCATTGGCAAAGAAACAA
synMUT4  ACCAGCAGCAGCCCCTGCATCCGGATGGGCAGCGTTGGCAAAGAAGCAG synMUT1  CTGAAGGCAAAAACCAGAAGACCTGATTGCACGCTCCAGAGCGGAT
synMUT2  CTCAAGGGGAAGAACCCTGAAGATCTATTGCACGCCCAGAGCGGCAT
synMUT3  CTGAACGGTAAAAATCCTGAAGATCTGATTGGCACACCAGCCGGAGCGGAT
synMUT4  CTGAACGCGAAACAACCCTGAAGCACCTGATCTGCACACCCGGAGCGAAT synMUT1  TTCAATCAAGCCCCTGTACAGCAAAAGGGGACATATGGATCTGCCAGAGG
synMUT2  CAGCCATCAAGCCTTTGTATTCCAAAAGGGACACCATGGATCTGCCTGAAG
synMUT3  TTCCATAAAACCTCTCTACTCTAAACGCGATACTATGGATCTGCCCGAGG
synMUT4  CTCGATCAAGCCACTGTACTCCAAAAGGGGACACCATGGACTTCGCTGAAG synMUT1  AACTGCCAGGAGTGAAGCCTTTCACCCGGCGGACCTTAGCCCAACTATGTAT
synMUT2  AATTGCCGGGCGTCAAACCATCCACACGGGCGCCATATCCAACCATGTAC
synMUT3  AATTGCCAGGAGTCGAAACCGTTTACAAAGGGCCCTACCCCACTATGTAC
synMUT4  AACTTCCGGGCGTGAAGCCTTTTACCCGGGCGCCATACCCAAGCAATGTAC synMUT1  AGCTTTTGGACCCTGACAATTCGGGAGTACGGCGGCTTCAGTACTCTGGA
synMUT2  ACCTTCCGGCCATCGACTATCAGACAGTATGCAGGCTTTAGCACTCTCGA
synMUT3  ACGTTCAGCCCTGACTATACGCCCAGTATGCCCGGATTTCTACCGCTTGA
synMUT4  ACTTTCCGCCCCGTGGACCATCAGACAGTACGCCCGGTTTCTCCACCGTCGA synMUT1  CGAATCAAACAAGTTTATAAGGACAAGCATCAAGCTGGACACAGGGCC
synMUT2  CGAATCCAATAAGTTCTATAAAGACAATATCAAAGCTGGCCAGCCAAGGTC
synMUT3  CGAATCCAACAAGTTTTATAAGGACAACATCAAAGCCGGGCAGCAGGGAC
synMUT4  AGAATCCAACAAGTTCTATAAGGACAACATCAAGCCCGGGCAGCAGGGAC synMUT1  TGAGTCTGGCATTCGATCTGGCCACACATGCGCGGCTATGACTCAGATAAT
synMUT2  TGTCCCGTGGCATTCGATCTGGCTACACATAGAGGTTATCATTCTGACAAT
synMUT3  TGTCAGTGGCATTTGATCTGGCCACCCACCGGGGTACCGACTCCGACAAC
synMUT4  TGAGCGGTCGCGCTTTGACCTGCCAACCCATCGGGGGTACGACTCCGACAAC synMUT1  CCCAGAGTCAGGGCGCACCGTGGGAATGGCACGACGCCTCGCTATCGACACAGT
synMUT2  CCAAGAGTACCGGCGAGCTGTCGGAATGGCGGAGTTGCCCATTGACACAGT
synMUT3  CCAAGAGTCGGGCCTGACCTCGGCCATGGCAGCGGTTGCCATTGACACAGT
synMUT4  CCTCGCGTGCCGGCGACCGTGGGAATGGCCGGAGTGGCTATCGACACCGT synMUT1  GGAAGATACTAAGATTCTGTTCGATCGAATCCCTCTGGAGAAATCTCTG    550
synMUT2  CGAGGACACCAAGATACTTTCGATGGGATTCCATTGGAGAAAATCTCTG
synMUT3  AGAGGATACTAAAATTTTGTTTGATGGGATCCCCCTAGAGAAGATCTCCG
synMUT4  CGAGGACACCAGATTCTCTTCGACGGAATCCCGCTGGAAAAGATCTCGG synMUT1  TGAGTATGACAATGAACGGGCTGTCATTCCCGTGCTGGCAAACTTCATC    600
synMUT2  TGTCAATGACGATGAACGGGCTGTCGATTCCCGTTTGGCGGAACTTCATC
synMUT3  TGTCTATGACGATGAACGGGCGCGTAATCCCAGTGCTTGCCAACTTCATA
synMUT4  TGTCCATGACGATGAATGGGCCCGTGATCCCGGTGCTCGCCGACTTCATC synMUT1  GTCACTGCCGAGGAACAGGGCGTGCCTAAGGCAAAAACTGACCGGCACAAT
synMUT2  GTCACCGGGGAAGAGCAGGGCGTCCCGAAGGAAAAGGTCACCGGGACAAT Figure 16 - continued

```
synMGT3      GTCACAGGGGAGGGCAGGGCGGTACCAAAGGAGAAGCTCACGGGGACAAT
synMGT4      GTGACGGGAGAGGAACAGGGAGTGCCGAAAGAGAAGCTGACCGGGACTAT
                  ** synMGT1      TCAGAACGGCATCCTGAAGGAGTTCATCGTGCCGAATACTTACTTTTTTC
synMGT2      CCAAAACGACATTCTTAAAGAATTCATGGTGAGAAATACCTACATCTTTC
synMGT3      CCAAAATGACATTCTGAAGGAATTCATGGTGAGAAATCCTTATATCTTTC
synMGT4      TCAGAATGACATCCTCAAGGCAGTTCATGGTCCCGCAACACTTACATTTTC
                 *     *  ***  *   *    **  * synMGT1      CCCCTGAAGCATCCATGAAAATCATTGCCGATATCTTCGGTACACGGCT
synMGT2      CTCCTGAGCCCTTCCATGAAGATCACGCGCGGACATCTTTGAATGCACGGCT
synMGT3      CTCCCGAGCCCTCTATGAAGATTATTGCCGACATTTTTGAATACACCGCA
synMGT4      CTCCTGGACCCTCGATGAAGATCATCGGTGCATGTTCGAGTACACCGCG
              *     ****        * synMGT1      AAGCACATGCCCAAGTTCAACTCAATTAGCATCTCCGGGTATCATATGCA
synMGT2      AAAACATGGCCTAAATTTAACTCAATCAGTATAAGCGGGTACCACATGCA
synMGT3      AAACATATGCCCAAGTTCAATTCCATATCTATTAGTGGATACCACATGCA
synMGT4      AAGCACATGCCGAAGTTCAACTCGGTCTCCATCTGGGGTACCACATGGA
              *  *    **  *  *  *     * synMGT1      GGAAGCAGGAGCCGACGGCTATTCTGGAGCTGGCTTACACCCTGGCAGATG
synMGT2      GGAGGCCGGCGCTGACGCTATACTTGAGCTCGCATATACCCTGGCAGATG
synMGT3      AGAAGCTGGGCTGATGCAATACTTGAGCTTGCCTACACCCTGGCCGACG
synMGT4      GGAGGCCGGGGCCGACGCCATTCTCGAACTGGCGTACACTCTGGCGGATG
              *    *             ***  * synMGT1      GCCTGCAATATTCTCGAACCGGACTGCAGGCCAGGGCTGACAATCGACGAG
synMGT2      GACTGGAATACTCCAAGGACCGGGCTCAGCCGCGGCTGACAGATCGACGAG
synMGT3      GACTGGAGTATTCTGCACTGGCCTGCAATCCGGCTGACAATGAGAGAG
synMGT4      GCCTGGAATACTCACGCACCGGCACTGCAGGCCCGACTGACAATCGACGAG
                             ******   * synMGT1      TTCGCTCCTAGACTGAGTTTTCTTTTCGGGGAATTGCCATGAACTTTTACAT
synMGT2      TTTGCCCCCTGACTCAGTTTTTCTCGGGGTATCGGGATGAATTTCTACAT
synMGT3      TTCGCCCCACGCCTTAGCTTCTTCTCGGGCATCGGCATCAATTTCTATAT
synMGT4      TTCGCCCCGACCGCTGTCCTTCTCTCGCCGGCATTGGGATGACTTTCTATAT
                *    *  *       *  *     **  *    ** synMGT1      GGAGATGGCTGAGATGAGGGCTGGCCCGAGGTGTGGGCACACCTGATGG
synMGT2      GGAGATAGCGAAGATGAGGCCGGCAGCGGGCTTTGGCGGCATCTGATGG
synMGT3      GGAGATCGCAAAGATGGAGGGCGGCCAGCCCACGCGCCCCATCTGATGG
synMGT4      GGAAATCGGGAAGATGAGAGCTGGAAGCGGCTGTGGGGCCACCTGATGG
             *   *  **             **   * synMGT1      AGAAGATGTTCCAGCCTAAGAACTCTAAGAGTCTGCTGCTGCGGGCCCAT
synMGT2      AGAAATGTTCCAGCCCAAGAATTCAAAGAGTCTGCTGTGAGAGCCAC
synMGT3      AAAAGATGTTTCAGCCTAAGAATAGTAAGAGCCTGCTCCTGCGGGCTCAC
synMGT4      AGAAGATGTTCCAGCCCAAGAACAGCAAAAGCCTTCTCCTCCGCGCCAC
             *  * * *        **  *   ** synMGT1      TGCCAGACATCCGGCTGCTCTCTGACTGAACAGGACCCATATAACAATAT      1100
synMGT2      TGCCAGACCTCAGCCTGGCACTGACTAACAGGACCCATACAACAACAT
synMGT3      TGTCAGAGCGTCAGGCTGGAGCCCTCACAGAGCAGGATCCTTACAATAACAT
synMGT4      TGCCAAACTTCCGGCTGGTCACTGACCGAGCAGGATCCGTACAACAACAT
                  *** synMGT1      TGTCAGAACCGCAATCGAGGCAATGGCAGCGGGTGTTCGGAGGAAACCCAGA
synMGT2      TGTTAGAACCGCCATCGAGGCGGATGGCAGCGGGTTTTCGGTGGGACACAGT
synMGT3      CGTCCCGACTGCTATTGAGCCCATGGCTGCAGTATTCGGAGGAACACAAA
synMGT4      TGTCCGGACTGCCATTGAGGCCATGGCCGCTGTGTTGGAGGCACTGAGT
                **  *            *  **  *  *  * synMGT1      GCCTGCACACAAACTCCCTTGATGCGGGCCCTGGGCTGCCTACCGTGAAG
synMGT2      CATTGCACACTAACTCATTGACGAAGCCCTCGGTCTGCCTACCGTGAAG
synMGT3      GCCTGCACACTAATTCTTTCGATGAGGCTTTGGGCTCCCTACCGTGAAG
synMGT4      CCCTCCACACTAACTCCTTCGACGAGGCCCTGGGTCTGCCGACCGTGAAG
                 ***  * **  *   **    *  **  *  ****** synMGT1      TCTCCTAGGATTCCACCCAATACACACATCATTATCCAGGAGGAGAATCCG
synMGT2      TCAGCTCGGATCCTAGGAACACAGCAGTCATCATCCAGGAGGAGAGTCG
synMGT3      TCAGCCAGAATTCCAAGAACACCCAAATATCATCCAACAGCAGATCAGC
synMGT4      TCCGCCCGGATAGCCAGAAATACTCAAATCATTATCCAGGAGCAAACGCG
```

```
synMUT2      CCTCGTTGCCAAAATGGGTCAGGACGGCCACGACCCGGCCGCCAAGTTA
synMUT3      TCTCGTCGGCAAAATGGGTCAGGACGGTCATCACCTGGCGGCCCAAGTCA
synMUT4      GCTCGTCGGCTAAAATGGGACAAGATGGGTCACCACCTGCGGCGCCAAGGTCA
                 ***          ** * synMUT1      TTGGCACGGGGTTCGCTGACCTGGGATTTGACGTGGATATCGGCCCTCTG
synMUT2      TCCCTACCGGTTTCGCTGACCTGGGCTTCGATGTGGATATCGGCACCACTG
synMUT3      TCCCAACGGGCTTCCCGATTTGGGCTTTGACGTGGATATCGGTCCCTTG
synMUT4      TGGCGGCTGGCTTCGGCGATCTGGATTCGACGTGGCATCGGACCTCTG
             *      *     *    *** synMUT1      TTCCAGACACCACGAGAGGGTGCACAGCAGGCAGTCGACGGCTGATGTGCA
synMUT2      TTTCAAACCCGCAGAGAAGTGCCTAACAAGCCGTTGACCCTGACGTACA
synMUT3      TTTCAAACCCCCAGGGAGGTGGCTCAGCAGGCTGTGGACCGCTGACGTCCA
synMUT4      TTTCAAACTCCGGGGGAAGTGGGCAGCAGGCGGGTGGACGCGACGTCGA
                   *        * synMUT1      CGCAGTCGAGTGTCCACTCTGGCAGCTGGCCATAAGACCCTGGTGCCTG
synMUT2      GGCTGTAGGCATCTCCATTCTGGCTGCCGSGGGATAAGACTCTCGTCCCBG
synMUT3      CGCAGTGGGCATTTCTACACTGGCAGCCCGGCACAAGACCTTCCTGCCAG
synMUT4      TGCCGTCGGGATGTCAACCCTTGGCGGCCGGCCATAAGACCCTGGTGCCGG
                     *    *     ** synMUT1      AACTGATCAAAGAGCTGAACTCTCTGGGCCAGACCAGACATCCTGGTCATG
synMUT2      AGCTGATAAAGGAGCTTAACAGCCTCGGAAGACCCGACATCCTGGTTATG
synMUT3      AACTGATCAAGGAGTTGAACAGCCTGGGACGCCCTGACATCCTGGTAATG
synMUT4      AACTGATCAAGGAGCTGAACTCGCTCGCGCGCCCGACATCCTCGTCATG
             * ***   *** * *** *     *  *** synMUT1      TGCGGCGGCGTGATCCCACCCCGGGATTACGAATTCCTGTTTGAGGTCGG
synMUT2      TGCGGGTGGAGTGATTCCGCCGCAGGATTACGAATTCCTCCTCTTGAAGTAGG
synMUT3      AACGGGTGGGGTAATCCCCCCCAAGACTACGAGTTCCTTTTTGAAGTGGG
synMUT4      TGTGGCGGAGTGATTCCGGCACAGGACTACGAGTTCCTGTTGGAAGTCGG
             *     *  *      *  **  * synMUT1      GGTGACCAACGTGTTCGGACCAGGAACCAGGATCCCTAAGGGCCCAGTGC
synMUT2      AGTGTAAACGTGTTCGGCCCAGGCACTCGGATACCAAGGCTGCCGTTC
synMUT3      TGTTCTAACGTGTTCGGACCTGGAACAAGAATCCCTAAGGCGGCCAGTGC
synMUT4      GGTGTCCAACGTCGTCGGTCCGGAACCAGAGTCGACGACGGTCGCCGTCC
                ******            ** synMUT1      AGGTCCTGGATGATATTGAAAAGTGTCTGGAAAAGAAACGGCAGTCAGTG    1250
synMUT2      AGGTGCTTGACCGCATTGAAAAGTCTCTGGACAAGAAGCCACGATCTGTG
synMUT3      AGGTGCTTGACGATATCGAGAAGTGCCTGGAGAAAAAGCAACAATCCGTT
synMUT4      AAGTGCTGGATGATATTGAGAAGTGCCTTGGGAAAAAGCAACAGTCAGTG
             *        *        * synMUT1      TAA
synMUT2      TAA
synMUT3      TAA
synMUT4      TGA
             *  *
```

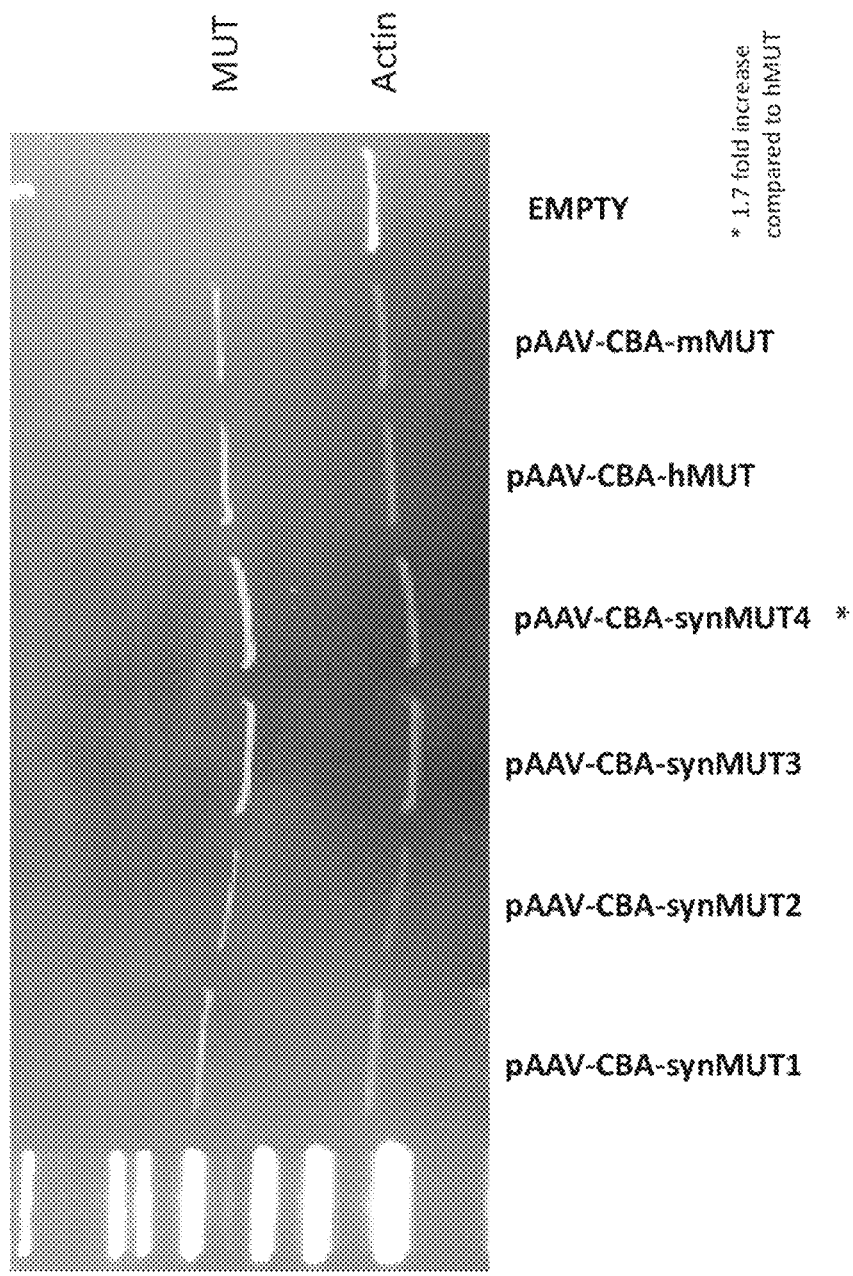

```
                        SEQUENCE LISTING

<160> NUMBER OF SEQ ID NOS: 6

<210> SEQ ID NO 1
<211> LENGTH: 2253
<212> TYPE: DNA
<213> ORGANISM: Artificial Sequence
<220> FEATURE:
<223> OTHER INFORMATION: synMUT1

<400> SEQUENCE: 1
atgctgagag ccaaaaacca gctgttcctg ctgagccccc actatctgag acaggtcaaa      60
gaaagttccg ggagtagact gatccagcag agactgctgc accagcagca gccactgcat     120
cctgagtggg ccgctctggc caagaaacag ctgaagggca aaaacccaga agacctgatc     180
tggcacactc cagagggggat ttcaatcaag cccctgtaca gcaaaaggga cactatggat     240
ctgccagagg aactgccagg agtgaagcct ttcacccgcg gaccttaccc aactatgtat     300 accttttcgac cctggacaat tcggcagtac gccggcttca gtactgtgga ggaatcaaac     360
aagttttata aggacaacat caaggctgga cagcagggcc tgagtgtggc attcgatctg     420
gccacacatc gcggctatga ctcagataat cccagagtca gggggggacgt gggaatggca     480 ggagtcgcta tcgacacagt ggaagatact aagattctgt tcgatggaat ccctctggag     540
aaaatgtctg tgagtatgac aatgaacggc gctgtcattc ccgtgctggc aaacttcatc     600
gtcactggcg aggaacaggg ggtgcctaag gaaaaactga ccggcacaat tcagaacgac     660
atcctgaagg agttcatggt gcggaatact tacattttc cccctgaacc atccatgaaa     720
atcattgccg atatcttcga gtacaccgct aagcacatgc ccaagttcaa ctcaattagc     780
atctccgggt atcatatgca ggaagcagga gccgacgcta ttctggagct ggcttacacc     840
ctggcagatg gcctggaata ttctcgaacc ggactgcagg caggcctgac aatcgacgag     900
ttcgctccta gactgagttt cttttgggga attggcatga acttttacat ggagatcgcc     960
aagatgaggg ctggccggag actgtgggca cacctgatcg agaagatgtt ccagcctaag    1020
aactctaaga gtctgctgct gcgggcccat tgccagacat ccggctggtc tctgactgaa    1080
caggacccat ataacaatat tgtcagaacc gcaatcgagg caatggcagc cgtgttcgga    1140
ggaacccaga gcctgcacac aaactccttt gatgaggccc tggggctgcc taccgtgaag    1200
tctgctagga ttgcacgcaa tacacagatc attatccagg aggaatccgg aatcccaaag    1260
gtggccgatc cctggggagg ctcttacatg atggagtgcc tgacaaacga cgtgtatgat    1320
gctgcactga gctgattaa tgaaatcgag gaaatggggg gaatggcaaa ggccgtggct    1380
gagggcattc caaaactgag gatcgaggaa tgtgcagcta ggcgccaggc acgaattgac    1440
tcaggaagcg aagtgatcgt cggggtgaat aagtaccagc tggagaaaga agacgcagtc    1500
gaagtgctgg ccatcgataa cacaagcgtg cgcaatcgac agattgagaa gctgaagaaa    1560
atcaaaagct cccgcgatca ggcactggcc gaacgatgcc tggcagccct gactgagtgt    1620
```

```
gctgcaagcg gggacggaaa cattctggct ctggcagtcg atgcctcccg ggctagatgc   1680
actgtggggg aaatcaccga cgccctgaag aaagtcttcg gagagcacaa ggccaatgat   1740
cggatggtga gcggcgctta tagacaggag ttcggggaat ctaaagagat taccagtgcc   1800
atcaagaggg tgcacaagtt catggagaga aagggcgac ggcccaggct gctggtggca    1860
aagatgggac aggacggaca tgatcgcgga gcaaaagtca ttgccaccgg gttcgctgac   1920
ctgggatttg acgtggatat cggccctctg ttccagacac cacgagaggt cgcacagcag   1980
gcagtcgacg ctgatgtgca cgcagtcgga gtgtccactc tggcagctgg ccataagacc   2040
ctggtgcctg aactgatcaa agagctgaac tctctgggca gaccagacat cctggtcatg   2100
tgcggcggcg tgatcccacc ccaggattac gaattcctgt ttgaggtcgg ggtgagcaac   2160
gtgttcggac caggaaccag gatccctaag gccgcagtgc aggtcctgga tgatattgaa   2220
aagtgtctgg aaaagaaaca gcagtcagtg taa                                2253
```

<210> SEQ ID NO 2
<211> LENGTH: 750
<212> TYPE: PRT
<213> ORGANISM: Homo sapiens

<400> SEQUENCE: 2

```
Met Leu Arg Ala Lys Asn Gln Leu Phe Leu Leu Ser Pro His Tyr Leu
1               5                   10                  15

Arg Gln Val Lys Glu Ser Ser Gly Ser Arg Leu Ile Gln Gln Arg Leu
                20                  25                  30

Leu His Gln Gln Gln Pro Leu His Pro Glu Trp Ala Ala Leu Ala Lys
            35                  40                  45

Lys Gln Leu Lys Gly Lys Asn Pro Glu Asp Leu Ile Trp His Thr Pro
        50                  55                  60

Glu Gly Ile Ser Ile Lys Pro Leu Tyr Ser Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
                100                 105                 110

Phe Ser Thr Val Glu Glu Ser Asn Lys Phe Tyr Lys Asp Asn Ile Lys
            115                 120                 125

Ala Gly Gln Gln Gly Leu Ser Val Ala Phe Asp Leu Ala Thr His Arg
        130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
                180                 185                 190

Ile Pro Val Leu Ala Asn Phe Ile Val Thr Gly Glu Glu Gln Gly Val
            195                 200                 205

Pro Lys Glu Lys Leu Thr Gly Thr Ile Gln Asn Asp Ile Leu Lys Glu
        210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255
```

-continued

```
Asn Ser Ile Ser Ile Ser Gly Tyr His Met Gln Glu Ala Gly Ala Asp
                260                 265                 270

Ala Ile Leu Glu Leu Ala Tyr Thr Leu Ala Asp Gly Leu Glu Tyr Ser
            275                 280                 285

Arg Thr Gly Leu Gln Ala Gly Leu Thr Ile Asp Glu Phe Ala Pro Arg
        290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Ile Gln Glu Ser
                405                 410                 415

Gly Ile Pro Lys Val Ala Asp Pro Trp Gly Gly Ser Tyr Met Met Glu
            420                 425                 430

Cys Leu Thr Asn Asp Val Tyr Asp Ala Ala Leu Lys Leu Ile Asn Glu
        435                 440                 445

Ile Glu Glu Met Gly Gly Met Ala Lys Ala Val Ala Glu Gly Ile Pro
    450                 455                 460

Lys Leu Arg Ile Glu Glu Cys Ala Ala Arg Arg Gln Ala Arg Ile Asp
465                 470                 475                 480

Ser Gly Ser Glu Val Ile Val Gly Val Asn Lys Tyr Gln Leu Glu Lys
                485                 490                 495

Glu Asp Ala Val Glu Val Leu Ala Ile Asp Asn Thr Ser Val Arg Asn
            500                 505                 510

Arg Gln Ile Glu Lys Leu Lys Lys Ile Lys Ser Ser Arg Asp Gln Ala
        515                 520                 525

Leu Ala Glu His Cys Leu Ala Ala Leu Thr Glu Cys Ala Ala Ser Gly
    530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
                565                 570                 575

Lys Ala Asn Asp Arg Met Val Ser Gly Ala Tyr Arg Gln Glu Phe Gly
            580                 585                 590

Glu Ser Lys Glu Ile Thr Ser Ala Ile Lys Arg Val His Lys Phe Met
        595                 600                 605

Glu Arg Glu Gly Arg Arg Pro Arg Leu Leu Val Ala Lys Met Gly Gln
    610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
                645                 650                 655

Val Ala Gln Gln Ala Val Asp Ala Asp Val His Ala Val Gly Val Ser
            660                 665                 670

Thr Leu Ala Ala Gly His Lys Thr Leu Val Pro Glu Leu Ile Lys Glu
```

|     | 675 |     |     | 680 |     |     | 685 |     |     |
|-----|-----|-----|-----|-----|-----|-----|-----|-----|-----|
| Leu | Asn | Ser | Leu | Gly | Arg | Pro | Asp | Ile | Leu | Val | Met | Cys | Gly | Gly | Val |

690 695 700

Ile Pro Pro Gln Asp Tyr Glu Phe Leu Phe Glu Val Gly Val Ser Asn
705 710 715 720

Val Phe Gly Pro Gly Thr Arg Ile Pro Lys Ala Ala Val Gln Val Leu
725 730 735

Asp Asp Ile Glu Lys Cys Leu Glu Lys Lys Gln Gln Ser Val
740 745 750

<210> SEQ ID NO 3
<211> LENGTH: 2253
<212> TYPE: DNA
<213> ORGANISM: Homo sapiens

<400> SEQUENCE: 3

```
atgttaagag ctaagaatca gcttttttta ctttcacctc attacctgag gcaggtaaaa      60
gaatcatcag gctccaggct catacagcaa cgacttctac accagcaaca gcccttcac     120
ccagaatggg ctgccctggc taaaaagcag ctgaaaggca aaacccaga gacctaata     180
tggcacaccc cggaagggat ctctataaaa cccttgtatt ccaagagaga tactatggac    240
ttacctgaag aacttccagg agtgaagcca ttcacgtg gaccatatcc taccatgtat     300
acctttaggc cctggaccat ccgccagtat gctggtttta gtactgtgga gaaaagcaat    360
aagttctata aggacaacat taaggctggt cagcaggat tatcagttgc ctttgatctg     420
gcgacacatc gtggctatga ttcagacaac cctcgagttc gtggtgatgt tggaatggct    480
ggagttgcta ttgacactgt ggaagatacc aaaattcttt ttgatggaat tcctttagaa    540
aaaatgtcag tttccatgac tatgaatgga gcagttattc agttcttgc aaattttata    600
gtaactggag aagaacaagg tgtacctaaa gagaagctta ctggtaccat ccaaaatgat    660
atactaaagg aatttatggt tcgaaataca tacatttttc ctccagaacc atccatgaaa    720
attattgctg acatatttga atatacagca agcacatgc caaaattta ttcaatttca    780
attagtggat accatatgca ggaagcaggg gctgatgcca ttctggagct ggcctatact    840
ttagcagatg gattggagta ctctagaact ggactccagg ctggcctgac aattgatgaa    900
tttgcaccaa ggttgtcttt cttctgggga attggaatga atttctatat ggaaatagca    960
aagatgagag ctggtagaag actctgggct cacttaatag agaaaatgtt tcagcctaaa   1020
aactcaaaat ctcttcttct aagagcacac tgtcagacat ctggatggtc acttactgag   1080
caggatccct acaataatat tgtccgtact gcaatagaag caatggcagc agtatttgga   1140
gggactcagt ctttgcacac aaattctttt gatgaagctt tgggtttgcc aactgtgaaa   1200
agtgctcgaa ttgccaggaa cacacaaatc atcattcaag aagaatctgg gattcccaaa   1260
gtggctgatc cttggggagg ttcttacatg atggaatgtc tcacaaatga tgtttatgat   1320
gctgctttaa agctcattaa tgaaattgaa gaaatgggtg aatggccaa agctgtagct   1380
gagggaatac ctaaacttcg aattgaagaa tgtgctgccc gaagacaagc tagaatagat   1440
tctggttctg aagtaattgt tggagtaaat aagtaccagt tggaaaaaga agacgctgta   1500
gaagttctgg caattgataa tacttcagtg cgaaacaggc agattgaaaa acttaagaag   1560
atcaaatcca gcagggatca agcttttggc gaacgttgtc ttgctgcact aaccgaatgt   1620
gctgctagcg gagatggaaa tatcctggct cttgcagtgg atgcatctcg ggcaagatgt   1680
acagtgggag aaatcacaga tgccctgaaa aaggtatttg gtgaacataa agcgaatgat   1740
```

```
cgaatggtga gtggagcata tcgccaggaa tttggagaaa gtaaagagat aacatctgct    1800
atcaagaggg ttcataaatt catggaacgt gaaggtcgca gacctcgtct tcttgtagca    1860
aaaatgggac aagatggcca tgacagagga gcaaaagtta ttgctacagg atttgctgat    1920
cttggttttg atgtggacat aggccctctt ttccagactc ctcgtgaagt ggcccagcag    1980
gctgtggatg cggatgtgca tgctgtgggc ataagcaccc tcgctgctgg tcataaaacc    2040
ctagttcctg aactcatcaa agaacttaac tcccttggac ggccagatat tcttgtcatg    2100
tgtggagggg tgataccacc tcaggattat gaatttctgt ttgaagttgg tgtttccaat    2160
gtatttggtc ctgggactcg aattccaaag gctgccgttc aggtgcttga tgatattgag    2220
aagtgtttgg aaaagaagca gcaatctgta taa                                 2253

<210> SEQ ID NO 4
<211> LENGTH: 2253
<212> TYPE: DNA
<213> ORGANISM: Artificial Sequence
<220> FEATURE:
<223> OTHER INFORMATION: SynMUT2

<400> SEQUENCE: 4
atgctgcgag cgaaaaatca gcttttctg ttgagcccac actacctgag gcaggttaaa       60
gaatccagcg ggagccggct gattcagcag cgactgctcc accagcagca gcctttgcat     120
cccgaatggg ctgctttggc gaagaagcag ctcaagggga gaaccctga agatcttatt      180 tggcacaccc cagagggcat cagcatcaag cctttgtatt ccaaaaggga caccatggat    240
ctgcctgaag aattgcccgg ggtcaaacca ttcacacggg ggccatatcc aaccatgtac    300
accttccggc catggactat cagacagtat gcaggcttta gcactgtcga ggaatccaat    360
aagttctata agacaatat caaagctggc cagcaaggtc tgtccgtggc attcgatctg    420
gctacacata gaggttatga ttctgacaat ccaagagtac ggggagacgt cggaatggcg    480
ggagttgcca ttgacacagt ggaggacacc aagatacttt tcgatgggat tccattggag    540
aaaatgtctg tgtcaatgac gatgaacggc gctgtgattc ccgttttggc gaacttcatc    600
gtcaccgggg aagagcaggg cgtcccgaag gaaaagctca ccgggacaat ccaaaacgac    660
attcttaaag aattcatggt gagaaatacc tacatctttc ctcctgagcc ttccatgaag    720
atcatcgcgg acatctttga atacacggct aaacacatgc taaatttaa ctcaatcagc     780 ataagcgggt accacatgca ggaggccggc gctgacgcta tacttgagct cgcatatacc    840
ctggcagatg gactggaata tcaaggacc gggctccagg ctggactgac aatcgacgag    900
tttgcccccc gactcagttt tttctggggt atcgggatga atttctacat ggagatagcg    960
aagatgaggg cgggcagacg gctttgggcg catctgatcg agaaaatgtt ccagcccaag    1020
aattcaaaga gtctgctgct gagagcccac tgccagacct caggctggag cctgactgaa    1080
caggacccat acaacaacat tgttagaacc gccatcgagg cgatggcagc ggttttcggt    1140
gggacacagt cattgcacac taactcattt gacgaagccc tcggtctgcc taccgtgaag    1200
tcagctcgga tcgctaggaa cacacagatc atcatccagg aggagagtgg catcccaaaa    1260
gtcgccgatc cttggggagg aagttacatg atggaatgcc tcacgaatga cgtatacgat    1320
gccgcactca agctgattaa cgagatcgag gaaatgggag gcatggcaaa agctgtcgcc    1380
gagggcattc caaagctgcg catagaggag tgtgccgccc gaagacaggc ccgcattgac    1440
tccggctctg aggtgatagt gggcgttaat aaatatcagc tagagaagga agacgccgtc    1500
```

```
gaagttctgg cgatagataa tacctctgtg cgaaatagac agattgagaa actgaagaag    1560
atcaagtcaa gccgagacca ggccttggcc gagaggtgtc tggcagccct cactgagtgc    1620
gcggcatctg gggacggcaa catattggca cttgccgtcg atgcctccag ggcccgatgt    1680
acggtcggcg aaattaccga tgccctcaag aaggttttg gcgagcacaa ggctaacgac     1740
aggatggtta gtggagcata cagacaggag tttggcgaaa gcaaggaaat tacttccgcg    1800
attaaaagag tgcacaaatt catggaacgg gagggtaggc gaccgaggct cctcgttgcc    1860
aaaatgggtc aggacggcca cgaccggggc gccaaggtta tcgctaccgg tttcgctgac    1920
ctgggcttcg atgtggatat cggaccactg tttcaaaccc ccagagaagt tgcccaacaa    1980
gccgttgacg ctgacgtaca cgctgtaggc atctccactc tcgccgccgg cataagact     2040 ctcgtcccag agctgataaa ggagcttaac agcctcggaa gacccgacat cctggttatg    2100
tgcggtggag tgattccgcc gcaggattac gaattcctct tcgaagtagg agtgtcaaac    2160
gtgttcggcc caggcactcg gatacccaag gctgccgttc aggtgcttga cgacattgaa    2220
aaatgtctgg agaagaagca acaatctgta taa                                 2253
```

<210> SEQ ID NO 5
<211> LENGTH: 2253
<212> TYPE: DNA
<213> ORGANISM: Artificial Sequence
<220> FEATURE:
<223> OTHER INFORMATION: SynMUT3

<400> SEQUENCE: 5

```
atgttgaggg ctaaaaacca gctctttctg ttgagtccac actaccttag caagtgaag      60 gaatctagcg gtagcaggct gatccagcag cgcctgctgc accagcagca gccctgcac     120 cctgagtggg ctgcattggc aaagaaacaa ctgaagggta aaatcctga agatctgatt     180 tggcacacac cggaggggat ttccataaaa cctctctact ctaaacgcga tactatggat    240
ctgcccgagc aattgccagg agtgaaaccc tttacaaggg ggccctaccc cactatgtac    300
acgttcagac cctggactat acgccagtat gccggatttt ctaccgttga ggaatccaac    360
aagttttata aggacaacat caaagccggg cagcagggac tgtcagtggc atttgatctc    420
gccacccacc gcgggtacga ctccgacaac ccaagagtcc gcggtgacgt cggcatggca    480
ggggttgcca ttgacacagt agaggatact aaaattttgt ttgatgggat ccccctagag    540
aagatgtccg tgtctatgac gatgaacggc gcggtaatcc cagtgcttgc caacttcata    600
gtcacagggg aagagcaggg cgtaccaaag gagaagctca caggaacaat ccaaaatgac    660
attctgaagg aattcatggt gagaaatact tatatctttc ctcccgagcc ctctatgaag    720
attattgccg acattttga atacaccgca aacatatgc ccaagttcaa ttccatatct      780
attagtggat accacatgca agaagctggg gctgatgcaa tacttgagct tgcctacacc    840
ctggccgacg gactgagta ttctcgcact ggcctgcaag ccgggctgac aattgacgag    900
ttcgccccac gccttagctt cttctgggc atcggcatga atttctatat ggagatcgca     960
aagatgagag cagggcggcg cttgtgggcc catctgatcg aaaagatgtt tcagcctaag    1020
aatagtaaga gcctgctcct gcgggctcac tgtcagacgt caggctggag cctcacagag    1080
caggatcctt acaataacat cgtccggact gctattgagg cgatggctgc agtattcgga    1140
ggaacacaaa gcctgcacac taattctttc gatgaggctt ggggctccc taccgtgaag    1200 tcagccagaa ttgcaagaaa cacccaaata atcatccaag aagaatcagg atcccaaaa    1260 gttgccgacc cctggggagg aagttatatg atggagtgcc tgaccaatga cgtctacgac    1320
```

```
gccgctttga agctgattaa cgagattgaa gagatgggcg gaatggccaa ggcggtcgct    1380
gagggcattc cgaaactgcg catagaggag tgtgctgctc gcaggcaggc cagaattgat    1440
tccggttccg aagtgatcgt gggggttaat aagtatcaac tggaaaaaga ggacgctgtc    1500
gaagtcctcg caatcgataa taccagcgtt agaaaccgac aaattgagaa gctgaaaaag    1560
atcaaaagtt caagggacca ggccttggct gagcggtgtc tcgccgcact gaccgaatgt    1620
gccgccagcg gcgatggtaa catcctcgcc ctcgctgtgg acgcttccag agcccggtgc    1680
accgtgggcg aaattacgga cgcgctgaaa aaagtctttg gcgaacacaa ggccaatgat    1740
agaatggtga gtggcgccta taggcaggag ttcggcgaga gtaaagaaat aacatccgcc    1800
atcaagaggg tccacaaatt tatggagcgg gaaggacgca gacctagact tctcgtggcc    1860
aaaatgggtc aggacggtca tgaccgggga gccaaagtca tcgcaacggg cttcgccgat    1920
ttggggtttg acgtggatat cggtcccttg tttcaaaccc ccagggaggt ggctcagcag    1980 gctgtgacg ctgacgtcca cgcagtgggc atttctacac tggcagccgg cacaagacg    2040 ttggtgccag aactgatcaa agagttgaac agcctgggac gccctgacat cctggtaatg    2100
tgcggtgggg taatcccccc ccaagactac gagttccttt cgaagtgggt gtttctaac    2160 gtgttcggac ctggaacaag aatccctaag gcggcagtgc aggtgcttga cgatatcgag    2220
aagtgcctgg agaaaaagca acaatccgtt taa                                2253

<210> SEQ ID NO 6
<211> LENGTH: 2253
<212> TYPE: DNA
<213> ORGANISM: Artificial Sequence
<220> FEATURE:
<223> OTHER INFORMATION: SynMUT4

<400> SEQUENCE: 6
atgcttcgcg ccaagaacca actgttcctg ctgtcccccc actacctccg acaagtcaag      60
gagagctcgg gaagccgcct gattcagcag cggctgctgc accagcagca gcccctgcat     120
ccggaatggg cagcgttggc aaagaagcag ctgaagggaa agaaccctga ggacctgatc     180
tggcacaccc cggagggaat ctcgatcaag ccactgtact ccaaaaggga caccatggac     240
ttgcctgaag aacttccggg cgtgaagcct tttacccggg ggccataccc aacaatgtac     300
actttccgcc cctggaccat cagacagtac gccggtttct ccaccgtcga agaatccaac     360
aagttctata aggacaacat caaggccggg cagcagggac tgagcgtcgc gtttgacctg     420
gcaacccatc gcggctacga ctccgacaac cctcgcgtgc gggggggacgt gggaatggcc     480 ggagtggcta tcgacaccgt ggaggacacc aagattctct tcgacggaat cccgctggaa     540
aagatgtcgt tgtccatgac catgaatggc gccgtgatcc cggtgctcgc gaacttcatc     600
gtgacgggag aggaacaggg agtgccgaaa gagaagctga ccgggactat tcagaatgac     660
atcctcaagg agttcatggt ccgcaacact tacattttcc ctcctgaacc ctcgatgaag     720
atcatcgctg acatcttcga gtacaccgcg aagcacatgc gaagttcaa ctcgatctcc     780 atctcgggct accacatgca ggaggccggg gccgacgcca ttctcgaact ggcgtacact     840
ctggcggatg gtctggaata tcacgcacc ggactgcagg ccggactgac aatcgacgag     900
ttcgccccga ggctgtcctt cttctggggc attgggatga acttctatat ggaaatcgcg     960
aagatgagag ctgaaggcg gctgtgggcg cacctgatcg agaagatgtt ccagcccaag    1020
aacagcaaaa gccttctcct ccgcgcccac tgccaaactt ccggctggtc actgaccgag    1080
```

```
caggatccgt acaacaacat tgtccggact gccattgagg ccatggccgc tgtgttcgga    1140
ggcactcagt ccctccacac taactccttc gacgaggccc tgggtctgcc gaccgtgaag    1200
tccgcccgga tagccagaaa tactcaaatc attatccagg aggaaagcgg aatccccaag    1260
gtcgccgacc cttggggagg atcttacatg atggagtgtt tgaccaatga cgtctacgac    1320
gccgccctga agctcattaa cgaaatcgaa gagatgggcg gaatggccaa ggccgtggct    1380
gagggcatcc cgaagctgag aatcgaggaa tgcgccgccc ggagacaggc ccgcattgat    1440
agcggcagcg aggtcattgt gggcgtgaac aagtaccagc ttgaaaagga ggacgccgtg    1500
gaagtgctgg caatcgataa cacctccgtg cgcaaccggc agatcgaaaa gctcaagaag    1560
attaagtcct cacgggacca ggcactggcg gagagatgcc tcgccgcgct gaccgaatgc    1620
gctgcctcgg gagatggcaa cattctggcc ctggcagtgg acgcctctcg ggctcggtgc    1680
actgtggggg agatcaccga cgccctcaag aaagtgttcg gtgaacataa ggccaacgac    1740
cggatggtgt ccggagcgta ccgccaggaa tttggcgaat caaaggaaat cacgtccgca    1800
atcaagaggg tgcacaaatt catggaacgg gagggcagac ggcccagact gctcgtggct    1860
aaaatgggac aagatggtca cgaccgcggc gccaaggtca tcgcgactgg cttcgccgat    1920
ctcggattcg acgtggacat cggacctctg tttcaaactc cccgggaagt ggcccagcag    1980
gccgtggacg cggacgtgca tgccgtcggg atctcaaccc tggcggccgg ccataagacc    2040
ctggtgccgg aactgatcaa ggagctgaac tcgctcggcc gccccgacat cctcgtgatg    2100
tgtggcggag tgattccgcc acaagactac gagttcctgt tcgaagtcgg ggtgtccaac    2160
gtgttcggtc ccggaaccag aatcccgaag gctgcggtcc aagtgctgga tgatattgag    2220
aagtgccttg agaaaaagca acagtcagtg tga                                2253
```

SYNTHETIC METHYLMALONYL-COA MUTASE TRANSGENE FOR THE TREATMENT OF MUT CLASS METHYLMALONIC ACIDEMIA (MMA)

PRIORITY DATA

This application is a continuation-in-part of U.S. patent application Ser. No. 14/773,885, filed Sep. 9, 2015, which is a national phase entry pursuant to 35 U.S.C. § 371 of International Patent Application No. PCT/US2014/028045, filed Mar. 14, 2014, which application claims the benefit of U.S. Provisional Application No. 61/792,081, filed Mar. 15, 2013, the entire disclosures of which are hereby incorporated by reference.

STATEMENT OF GOVERNMENT INTEREST

The instant application was made with government support; the government has certain rights in this invention.

SEQUENCE LISTING DATA

The Sequence Listing text document filed herewith, created Mar. 10, 2016, size 22 kilobytes, and named "6137NHGRI-6-PUS-C1_Sequence_Listing_ST25.txt," is incorporated herein by reference in its entirety.

FIELD OF THE INVENTION

The subject invention relates to engineering of the human methylmalonyl-coA mutase gene so as to enhance its expression in eukaryotic cells. Compared to the natural human MUT gene, the subject synthetic gene sequences (synMUT) are codon-optimized to enhance expression upon administration.

BACKGROUND

Methylmalonic acidemia (MMA) is an autosomal recessive disorder caused by defects in the mitochondrial localized enzyme methylmalonyl-CoA mutase (MUT) (Manoli, et al. 2010 Methylmalonic Acidemia (in *Gene Reviews*, eds. Pagon, et al.)). The estimated incidence of MMA is 1 in 25,000-48,000. MUT is an enzyme that catalyzes the conversion of L-methylmalonyl-CoA to succinyl-CoA. This reaction is one of several enzymatic reactions required to metabolize branch chain amino acids, odd chain fatty acids, and propionate produced by the gut flora (Chandler, et al. 2005 *Mol Genet Metab* 86:34-43). MUT deficiency, the most common cause of MMA, is characterized by the accumulation of methylmalonic acid and other disease-related metabolites. The disease is managed with dietary restriction of amino acid precursors and cofactors but lacks definitive therapy. MMA can lead to metabolic instability, seizures, strokes, and kidney failure, and it can be lethal even when patients are being properly managed, underscoring the need for new therapies for this disease. Even though MMA is rare, all babies born in the USA are screened for this condition as newborns, emphasizing the need to develop better therapies.

SUMMARY

As discussed above, the only treatments for MMA currently available are dietary restrictions. Patients still become metabolically unstable while on diet restriction and experience disease progression, despite medical therapy. These episodes result in numerous hospitalizations and can be fatal. The synthetic human methylmalonyl-CoA mutase (synMUT) transgene can be used as a drug, via viral- or non-viral mediated gene delivery, to restore MUT function in MMA patients, prevent metabolic instability, and ameliorate disease progression. Because this enzyme may also be important in other disorders of branched chain amino acid oxidation, gene delivery of synthetic MUT gene could be used to treat conditions other than MUT MMA.

Additionally, the synMUT transgene can be used for the in vitro production of MUT for use in enzyme replacement therapy for MMA. Enzyme replacement therapy is accomplished by administration of the synthetic MUT protein orally, sub-cutaneously, intra-muscularly, intravenously, or by other therapeutic delivery routes.

Thus, in one aspect, the invention is directed to a synthetic methylmalonyl-CoA mutase (MUT) polynucleotide (synMUT) selected from the group consisting of:
a) a polynucleotide comprising a polynucleotide selected from the group consisting of the nucleic acid sequence of SEQ. ID NO:1, SEQ ID NO:4, SEQ ID NO:5, and SEQ ID NO:6;
b) a polynucleotide having the nucleic acid sequence of SEQ ID NO:1, SEQ ID NO:4, SEQ ID NO:5, or SEQ ID NO:6;
c) a polynucleotide having a nucleic acid sequence with at least about 80% identity to the nucleic acid sequence of SEQ ID NO:1, SEQ ID NO:4, SEQ ID NO:5, or SEQ ID NO:6 and having at least equivalent expression as SEQ ID NO:1, SEQ ID NO:4, SEQ ID NO:5, or SEQ ID NO:6 in a subject;
d) a polynucleotide encoding a polypeptide having the amino acid sequence of SEQ ID NO:3 or an amino acid sequence substantially identical to the amino acid sequence of SEQ ID NO:3, wherein the polynucleotide does not have the nucleic acid sequence of SEQ ID NO:3; and
e) a polynucleotide encoding an active fragment of the methylmalonyl-CoA mutase (MUT) protein, wherein the polynucleotide in its entirety does not share 100% identity with a portion of the nucleic acid sequence of SEQ ID NO:3.

In one embodiment, the fragment includes only amino acid residues 33-750, which is encoded between nucleotides 63-2250 in synMUT, and which represents the active, processed form of MUT.

By active can be meant, for example, the enzyme's ability to catalyze the isomerization of methylmalonyl-CoA to succinyl-CoA. The activity can be assayed using methods well-known in the art (as described in the context of protein function, below).

In one embodiment of a synthetic polynucleotide according to the invention, the nucleic acid sequence encodes a polypeptide having the amino acid sequence of SEQ ID NO:2 or an amino acid sequence with at least about 90% identity to the amino acid sequence of SEQ ID NO:2.

In another embodiment, the synthetic polynucleotide exhibits augmented expression relative to the expression of naturally occurring human methylmalonyl-CoA mutase polynucleotide sequence (SEQ ID NO:3) in a subject. In another embodiment, the synthetic polynucleotide of the invention exhibits therapeutically useful expression in a subject. The expression level of the MUT polypeptide is optionally at a level that provides for a clinically observable level of MUT activity in a subject. In yet another embodiment, the synthetic polynucleotide comprises a nucleic acid sequence comprising codons that have been optimized relative to the naturally occurring human methylmalonyl-CoA mutase polynucleotide sequence (SEQ ID NO:3). In still another embodiment of a synthetic polynucleotide according to the invention, the nucleic acid sequence has at least about 80% of less commonly used codons replaced with more commonly used codons.

In one embodiment of a synthetic polynucleotide according to the invention, the polynucleotide is a polynucleotide having a nucleic acid sequence with at least about 85% identity to the nucleic acid sequence of SEQ ID NO:1, SEQ ID NO:4, SEQ ID NO:5, or SEQ ID NO:6. In another embodiment, the polynucleotide is a polynucleotide having a nucleic acid sequence with at least about 90% identity to the nucleic acid sequence of SEQ ID NO:1, SEQ ID NO:4, SEQ ID NO:5, or SEQ ID NO:6. In still another embodiment, the polynucleotide is a polynucleotide having a nucleic acid sequence with at least about 95% identity to the nucleic acid sequence of SEQ ID NO:1, SEQ ID NO:4, SEQ ID NO:5, or SEQ ID NO:6.

In one embodiment of a synthetic polynucleotide according to the invention, the nucleic acid sequence is a DNA sequence. In another embodiment, the nucleic acid sequence is a RNA sequence or peptide modified nucleic acid sequence. In another embodiment, the synthetic polynucleotide according to the invention encodes an active MUT fragment, amino acids 33-750 of MUT, corresponding to base pairs 67-2250 in synMUT.

In another aspect, the invention is directed to an expression vector comprising the herein-described synthetic polynucleotide. In another embodiment of a vector according to the invention, the synthetic polynucleotide is operably linked to an expression control sequence. In still another embodiment, the synthetic polynucleotide is codon-optimized.

In a further aspect, the invention is directed to a method of treating a disease or condition mediated by methylmalonyl-CoA mutase or low levels of methylmalonyl-CoA mutase activity, the method comprising administering to a subject the herein-described synthetic polynucleotide.

In still a further aspect, the invention is directed to a method of treating a disease or condition mediated by methylmalonyl-CoA mutase, the method comprising administering to a subject a methylmalonyl-CoA mutase produced using the synthetic polynucleotide described herein. In another embodiment of a method of treatment according to the invention, the disease or condition is methylmalonic acidemia (MMA).

In one aspect, the invention is directed to a composition comprising the synthetic polynucleotide of claim 1 and a pharmaceutically acceptable carrier.

In another aspect, the invention is directed to a transgenic animal whose genome comprises a polynucleotide sequence encoding methylmalonyl-CoA mutase or a functional fragment thereof. In still another aspect, the invention is directed to a method for producing such a transgenic animal, comprising: providing an exogenous expression vector comprising a polynucleotide comprising a promoter operably linked to a polynucleotide encoding methylmalonyl-CoA mutase or a functional fragment thereof; introducing the vector into a fertilized oocyte; and transplanting the oocyte into a female animal.

In one aspect, the invention is directed to a transgenic animal whose genome comprises the synthetic polynucleotide described herein. In another aspect, the invention is directed to a method for producing such a transgenic animal, comprising: providing an exogenous expression vector comprising a polynucleotide comprising a promoter operably linked to the synthetic polynucleotide described herein; introducing the vector into a fertilized oocyte; and transplanting the oocyte into a female animal.

Methods for producing transgenic animals are known in the art and include, without limitation, transforming embryonic stem cells in tissue culture, injecting the transgene into the pronucleus of a fertilized animal egg (DNA microinjection), genetic/genome engineering, viral delivery (for example, retrovirus-mediated gene transfer).

Transgenic animals according to the invention include, without limitation, rodent (mouse, rat, squirrel, guinea pig, hamster, beaver, porcupine), frog, ferret, rabbit, chicken, pig, sheep, goat, cow primate, and the like.

In another aspect, the invention is directed to the preclinical amelioration or rescue from the disease state, for example, methylmalonic acidemia, that the afflicted subject exhibits. This may include symptoms, such as lethargy, lethality, metabolic acidosis, and biochemical perturbations, such as increased levels of methylmalonic acid in blood, urine, and body fluids.

In still another aspect, the invention is directed to a method for producing a genetically engineered animal as a source of recombinant synMUT. In another aspect, genome editing, or genome editing with engineered nucleases (GEEN) may be performed with the synMUT nucleotides of the present invention allowing synMUT DNA to be inserted, replaced, or removed from a genome using artificially engineered nucleases. Any known engineered nuclease may be used such as Zinc finger nucleases (ZFNs), Transcription Activator-Like Effector Nucleases (TALENs), the CRISPR/Cas system, and engineered meganuclease re-engineered homing endonucleases. Alternately, the nucleotides of the present invention including synMUT, in combination with a CASP/CRISPR, ZFN, or TALEN can be used to engineer correction at the locus in a patient's cell either in vivo or ex vivo, then, in one embodiment, use that corrected cell, such as a fibroblast or lymphoblast, to create an iPS or other stem cell for use in cellular therapy.

BRIEF DESCRIPTION OF THE DRAWINGS

FIG. 1 illustrates the list of codon frequencies in the human proteome.

FIG. 2 illustrates a codon-optimized synMUT (SEQ ID NO:1) of the subject invention.

FIG. 3 illustrates naturally occurring *Homo sapiens* MUT amino acid sequence (SEQ ID NO:2) and naturally occurring *Homo sapiens* MUT gene (SEQ ID NO:3).

FIG. 4 illustrates an alignment of MUT (SEQ ID NO:3) with the subject codon-optimized synMUT sequence (SEQ ID NO:1).

FIG. 5 illustrates the exonic variants seen in MUT that are present in synMUT. The numeral 1 displayed indicate changes seen in MUT in an exome analysis that are found in synMUT. The numeral 2 displayed in the figure indicates unique synMUT variants at a position where MUT variants exist.

FIG. 12 shows a summary of the CLUSTAL W (1.83) multiple sequence alignment of wild type human MUT (hMUT)(SEQ ID NO:3) compared to synthetic, codon optimized MUT alleles (synMUT1-4)(SEQ ID NO:1, SEQ ID NO:4, SEQ ID NO:5, SEQ ID NO:6, respectively) depicted as percent identity to hMUT.

FIG. 13 shows a summary of the CLUSTAL W (1.83) multiple sequence alignment synthetic, codon optimized MUT alleles (synMUT1-4)(SEQ ID NO:1, SEQ ID NO:4, SEQ ID NO:5, SEQ ID NO:6, respectively) depicted as percent identity to synMUT1 (SEQ ID NO:1).

FIG. 15 shows CLUSTAL W (1.83) multiple sequence alignment of wild type human MUT (hMUT) (SEQ ID NO:3) compared to synthetic, codon optimized MUT alleles (synMUT1-4) (SEQ ID NO:1, SEQ ID NO:4, SEQ ID NO:5, SEQ ID NO:6). An asterisk indicates a conserved base, with the numbering beginning at the first base pair of the coding sequence.

FIG. 16 shows CLUSTAL W (1.83) multiple sequence alignment of synthetic, codon optimized MUT alleles (synMUT1-4) (SEQ ID NO:1, SEQ ID NO:4, SEQ ID NO:5, SEQ ID NO:6). An asterisk indicates a conserved base, with the numbering beginning at the first base pair of the coding sequence.

FIG. 17 shows a Western blot analysis of MUT expression in 293T cells.

DETAILED DESCRIPTION

Figure 6:
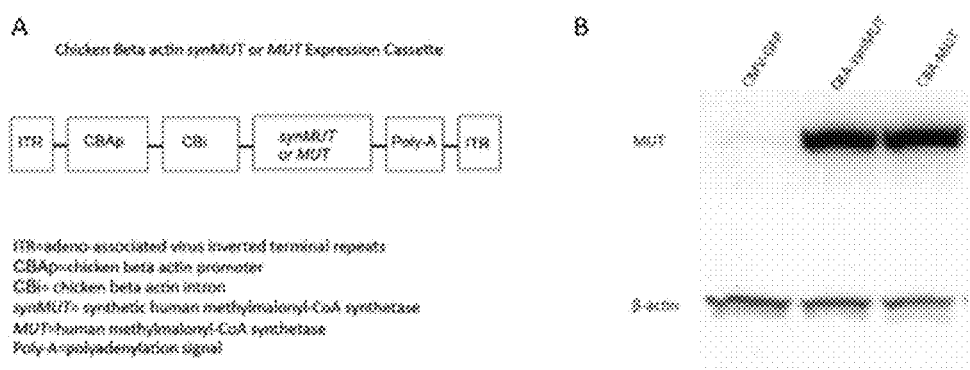
FIG. 6 illustrates the expression of MUT protein following transfection of HEK-293 cells in vitro with green fluorescent protein (GFP), optimized human methylmalonyl-CoA mutase polynucleotide (synMUT) (SEQ ID NO:1), or naturally-occurring human methylmalonyl-CoA mutase gene (MUT) (SEQ ID NO:3).

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Definitions

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices, and materials are now described.

As used in this application, including the appended claims, the singular forms "a," "an," and "the" include plural references, unless the content clearly dictates otherwise, and are used interchangeably with "at least one" and "one or more." Thus, reference to "a polynucleotide" includes a plurality of polynucleotides or genes, and the like.

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

In the context of synMUT, the terms "gene" and "transgene" are used interchangeably. A "transgene" is a gene that has been transferred from one organism to another.

The term "subject", as used herein, refers to a domesticated animal, a farm animal, a primate, a mammal, for example, a human.

The phrase "substantially identical", as used herein, refers to an amino acid sequence exhibiting high identity with a reference amino acid sequence (for example, at least 80%, at least 85%, at least 90%, at least 95%, at least 98%, or at least 99% identity) and retaining the biological activity of interest (the enzyme activity).

The polynucleotide sequences encoding synMUT allow for, example, equivalent or increased expression of the synMUT gene relative to naturally occurring human MUT sequences. Alternatively, the synthetic polynucleotides of the invention exhibit therapeutically useful and/or clinically observable expression in a subject. These polynucleotide sequences are designed to not alter the naturally occurring human MUT amino acid sequence. They are also engineered or optimized to have increased transcriptional, translational, and protein refolding efficacy. This engineering is accomplished by using human codon biases, evaluating GC, CpG, and negative GpC content, optimizing the interaction between the codon and anti-codon, and eliminating cryptic splicing sites and RNA instability motifs. Because the sequences are novel, they facilitate detection using nucleic acid-based assays.

As used herein, "MUT" refers to human methylmalonyl coenzyme A mutase, and "Mut" refers to mouse methylmalonyl coenzyme A mutase. This protein catalyzes the isomerization of methylmalonyl-CoA to succinyl-CoA. This process requires 5'-deoxyadenosylcobalamin, a vitamin B 12 derivative. Succinyl-CoA is a component of the citric acid cycle or tricarboxylic acid cycle (TCA). The gene encoding naturally occurring human methylmalonyl coenzyme A mutase gene is referred to as MUT. The polynucleotide encoding synthetic MUT is known as synMUT.

Naturally occurring human MUT is referred to as MUT, while synthetic MUT disclosed herein are designated as synMUT, synMUT1, synMUT2, synMUT3, and/or synMUT4, even though the two are identical at the amino acid level.

"Codon optimization" refers to the process of altering a naturally occurring polynucleotide sequence to enhance expression in the target organism, e.g., humans. In the subject application, the human MUT gene has been altered to replace codons that occur less frequently in human genes with those that occur more frequently and/or with codons that are frequently found in highly expressed human genes.

As used herein, "determining", "determination", "detecting", or the like are used interchangeably herein and refer to the detecting or quantitation (measurement) of a molecule using any suitable method, including immunohistochemistry, fluorescence, chemiluminescence, radioactive labeling, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like. "Detecting" and its variations refer to the identification or observation of the presence of a molecule in a biological sample, and/or to the measurement of the molecule's value.

As used herein, a "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In certain embodiments, it may be preferable to include isotonic agents, for example, sugars, polyalcohols such as mannitol, sorbitol, or sodium chloride in the composition.

A "therapeutically effective amount" refers to an amount effective, at dosages and for periods of time necessary, to achieve the desired therapeutic result. A therapeutically effective amount of a vector comprising the synthetic polynucleotide of the invention may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the synthetic polynucleotide or a fragment thereof according to the invention calculated to produce the desired therapeutic effect in association with a pharmaceutical carrier.

In one embodiment of the invention, codon optimization was employed to create highly active and synthetic MUT alleles. This method involves determining the relative frequency of a codon in the protein-encoding genes in the human genome. For example, isoleucine can be encoded by AUU, AUC, or AUA, but in the human genome, AUC (47%), AUU (36%), and AUA (17%) are variably used to encode isoleucine in proteins. Therefore, in the proper sequence context, AUA would be changed to AUC to allow this codon to be more efficiently translated in human cells. FIG. 1 presents the codon usage statistics for a large fraction of human protein-encoding genes and serves as the basis for changing the codons throughout the MUT cDNA.

Thus, the invention comprises synthetic polynucleotides encoding methylmalonyl-CoA mutase (MUT) selected from the group consisting of the nucleic acid sequence of FIG. 2 (SEQ ID NO:1), SEQ ID NO:4, SEQ ID NO:5, SEQ ID NO:6, and a polynucleotide sequence having at least about 80% identity thereto. For those polynucleotides having at least about 80% identity to SEQ ID NO:1, SEQ ID NO:4, SEQ ID NO:5, SEQ ID NO:6, in additional embodiments, they have at least 85%, at least 90%, at least 95%, at least 97%, at least 98%, or at least 99% identity thereto. In one embodiment, the polynucleotide does not have the nucleic acid sequence of SEQ ID NO:3. In another embodiment, the polynucleotide has at least equivalent expression in a host as SEQ ID NO:3. In another embodiment, the synthetic polynucleotide of the invention exhibits therapeutically useful expression in a subject. The expression level of the MUT polypeptide is optionally at a level that provides for a clinically observable level of MUT activity in a subject.

In one embodiment, the subject synthetic polynucleotide encodes a polypeptide with 100% identity to the naturally occurring human MUT protein, alternatively including naturally occurring alleles (FIG. 3). BLASTN alignment of MUT (NM_000255.3)(SEQ ID NO:3) with synMUT1 (SEQ ID NO:1) reveals 1721/2253 (76%) identities (FIG. 4); 532 bases are present in synMUT1 (SEQ ID NO:1) and not in MUT (NM_000255.3)(SEQ ID NO:3) (FIG. 4). To further validate that the synMUT1 sequence selected was sufficiently unique, 8600 exomes deposited in the NHLBI exome variant server (http://evs.gs.washington.edu/EVS/) were analyzed using NCBI's Align Specialized BLAST to compare the two sequences. 67 naturally occurring nucleotide changes in the MUT coding sequence resulted in synonymous alleles, missense variants, and missense mutations (Table 1). At nine of these 67 variant locations, synMUT possessed unique nucleotides that were not present in the exome database (FIG. 5). The synMUT therefore encodes 58 variants, present at variable frequencies (Table 1), identified in the exome database, and 474 unique base pairs, not present in the 8600 human exomes compared to MUT (NM_000255.3).

TABLE 1

Variants in syn-MUT not observed in the Exome data base

| Variant Position | Allelles Non-Coding Strand Bases | Allele Present on Coding Strand syn-MUT | All Allele # | MAF (%) | GVS Function | Amino Acid | Protein Pos. | cDNA Pos. |
|---|---|---|---|---|---|---|---|---|
| 6:49427127 | C/T | A | C = 1/T = 13005 | 0.0116/0.0/0.0077 | missense | ARG, GLN | 18/751 | 53 |
| 6:49427030 | G/C | G | G = 1/C = 13005 | 0.0/0.0227/0.0077 | missense | HIS, GLN | 50/751 | 150 |
| 6:49426975 | C/T | A | C = 39/T = 12967 | 0.3837/0.1362/0.2999 | missense | VAL, ILE | 69/751 | 205 |
| 6:49426939 | G/A | C | G = 1/A = 13005 | 0.0116/0.0/0.0077 | coding-synonymous | none | 81/751 | 241 |
| 6:49426895 | C/T | T | C = 3/T = 13003 | 0.0/0.0681/0.0231 | coding-synonymous | none | 95/751 | 285 |
| 6:49426896 | A/G |  | A = 3/G = 13003 | 0.0/0.0681/0.0231 | missense | LEU, PRO | 95/751 | 284 |
| 6:49426853 | T/C | G | T = 1/C = 13005 | 0.0116/0.0/0.0077 | coding-synonymous | none | 109/751 | 327 |
| 6:49426814 | C/G | T | C = 1/G = 13005 | 0.0116/0.0/0.0077 | missense | LEU, PHE | 122/751 | 366 |
| 6:49425764 | T/C | G | T = 15/C = 12989 | 0.0/0.3404/0.1153 | coding-synonymous | none | 131/751 | 393 |
| 6:49425601 | C/T | A | C = 1/T = 13005 | 0.0116/0.0/0.0077 | missense | VAL, MET | 186/751 | 556 |
| 6:49425591 | C/T | A | C = 3/T = 13003 | 0.0/0.0681/0.0231 | missense | SER, ASN | 189/751 | 566 |
| 6:49425537 | A/C | G | A = 1/C = 13005 | 0.0/0.0227/0.0077 | missense | VAL, GLY | 207/751 | 620 |
| 6:49425521 | T/C | A | T = 7823/C = 5181 | 38.3578/42.7372/39.8416 | coding-synonymous | none | 212/751 | 636 |
| 6:49425446 | C/T | A | C = 138/T = 12854 | 1.3388/0.5225/1.0622 | coding-synonymous | none | 237/751 | 711 |
| 6:49425436 | C/T | A | C = 1/T = 12995 | 0.0/0.0227/0.0077 | missense | VAL, ILE | 241/751 | 721 |
| 6:49423948 | A/G | C | A = 1/G = 13003 | 0.0116/0.0/0.0077 | coding-synonymous | none | 252/751 | 756 |
| 6:49423923 | C/T | A | C = 1/T = 13005 | 0.0/0.0227/0.0077 | missense | VAL, ILE | 261/751 | 781 |
| 6:49423868 | C/T | A | C = 12/T = 12994 | 0.0/0.2724/0.0923 | missense | CYS, TYR | 279/751 | 836 |
| 6:49423826 | C/T | A | C = 13/T = 12993 | 0.1395/0.0227/0.1 | missense | ARG, GLN | 293/751 | 878 |
| 6:49421373 | T/C | G | T = 2/C = 13004 | 0.0/0.0454/0.0154 | missense | ILE, MET | 336/751 | 1008 |
| 6:49421345 | T/G | C | T = 1/G = 13005 | 0.0/0.0227/0.0077 | missense | ILE, LEU | 346/751 | 1036 |
| 6:49419403 | G/T | A | G = 1/T = 13005 | 0.0/0.0227/0.0077 | missense | PRO, THR | 370/751 | 1108 |
| 6:49419396 | G/A | T | G = 6/A = 13000 | 0.0698/0.0/0.0461 | missense | THR, ILE | 372/751 | 1115 |
| 6:49419386 | T/C | G | T = 22/C = 12984 | 0.2442/0.0227/0.1692 | missense | ILE, MET | 375/751 | 1125 |
| 6:49419305 | C/A | T | C = 1/A = 13005 | 0.0/0.0227/0.0077 | coding-synonymous | none | 402/751 | 1206 |
| 6:49419241 | A/G | C | A = 1/G = 13005 | 0.0/0.0227/0.0077 | missense | SER, PRO | 424/751 | 1272 |
| 6:49419214 | G/A | T | G = 1/A = 13005 | 0.0116/0.0/0.0077 | missense | ARG, CYS | 433/751 | 1297 |
| 6:49419206 | A/T | A | A = 1/T = 13005 | 0.0116/0.0/0.0077 | coding-synonymous | none | 435/751 | 1305 |
| 6:49416573 | T/C | G | T = 1/C = 13005 | 0.0116/0.0/0.0077 | missense | GLN, ARG | 467/751 | 1400 |
| 6:49416571 | C/T | A | C = 1/T = 13005 | 0.0116/0.0/0.0077 | missense | VAL, ILE | 468/751 | 1402 |
| 6:49416556 | A/C | G | A = 2/C = 13004 | 0.0233/0.0/0.0154 | missense | SER, ALA | 473/751 | 1417 |
| 6:49416552 | T/C | G | T = 1/C = 13005 | 0.0/0.0227/0.0077 | missense | GLN, ARG | 474/751 | 1421 |
| 6:49415450 | C/T | A | C = 1/T = 12997 | 0.0116/0.0/0.0077 | missense | GLY, ASP | 498/751 | 1493 |
| 6:49415448 | T/C | G | T = 1343/C = 11655 | 10.5655/9.8774/10.3324 | missense | THR, ALA | 499/751 | 1495 |
| 6:49415432 | C/G | C | C = 1/G = 12999 | 0.0/0.0227/0.0077 | missense | GLY, ALA | 504/751 | 1511 |
| 6:49415384 | G/T | A | G = 1/T = 12997 | 0.0116/0.0/0.0077 | missense-near-splice | THR, LYS | 520/751 | 1559 |
| 6:49412463 | C/T | A | C = 1/T = 13005 | 0.0116/0.0/0.0077 | missense | ARG, LYS | 522/751 | 1566 |
| 6:49412458 | C/T | T | C = 1/T = 13005 | 0.0116/0.0/0.0077 | missense | GLY, SER | 524/751 | 1570 |
| 6:49412433 | T/C | G | T = 4077/C = 8929 | 36.6047/21.0849/31.3471 | missense | HIS, ARG | 532/751 | 1595 |
| 6:49412430 | T/C | G | T = 1/C = 13005 | 0.0116/0.0/0.0077 | missense | TYR, CYS | 533/751 | 1598 |
| 6:49412421 | A/G | C | A = 1/G = 13005 | 0.0/0.0227/0.0077 | missense | VAL, ALA | 536/751 | 1607 |
| 6:49412399 | A/G | C | A = 56/G = 12950 | 0.6047/0.0908/0.4306 | coding-synonymous | none | 543/751 | 1629 |
| 6:49412398 | T/C | G | T = 1/C = 13005 | 0.0/0.0227/0.0077 | missense | ARG, GLY | 544/751 | 1630 |
| 6:49409627 | T/C | C | T = 1/C = 13005 | 0.0/0.0227/0.0077 | coding-synonymous | none | 578/751 | 1734 |
| 6:49409598 | A/C | G | A = 3/C = 13003 | 0.0/0.0681/0.0231 | missense | LEU, ARG | 588/751 | 1763 |
| 6:49409599 | A/G | A | A = 16/G = 12990 | 0.0/0.3631/0.123 | missense | CYS, ARG | 588/751 | 1762 |
| 6:49409584 | G/C | G | G = 2/C = 13004 | 0.0/0.0454/0.0154 | missense | GLN, GLU | 593/751 | 1777 |
| 6:49409569 | C/T | A | C = 2/T = 13004 | 0.0/0.0454/0.0154 | missense | ALA, THR | 598/751 | 1792 |
| 6:49408037 | T/C | A | T = 1/C = 13005 | 0.0/0.0227/0.0077 | missense | HIS, ARG | 613/751 | 1839 |
| 6:49408008 | T/C | G | T = 1/C = 13005 | 0.0/0.0227/0.0077 | missense | ARG, GLY | 623/751 | 1867 |
| 6:49407995 | C/T | A | C = 1/T = 13005 | 0.0116/0.0/0.0077 | missense | ARG, HIS | 627/751 | 1880 |
| 6:49407986 | T/C | G | T = 1/C = 13005 | 0.0116/0.0/0.0077 | missense | GLU, GLY | 630/751 | 1889 |
| 6:49403334 | G/A | A | G = 1/A = 13005 | 0.0116/0.0/0.0077 | coding-synonymous | none | 653/751 | 1959 |
| 6:49403324 | A/C | G | A = 1/C = 13005 | 0.0/0.0227/0.0077 | missense | LEU, VAL | 657/751 | 1969 |
| 6:49403301 | T/C | T | T = 21/C = 12985 | 0.0465/0.3858/0.1615 | coding-synonymous | none | 664/751 | 1992 |
| 6:49403302 | A/G | C | A = 6/G = 13000 | 0.0698/0.0/0.0461 | missense | VAL, ALA | 664/751 | 1991 |

TABLE 1-continued

Variants in syn-MUT not observed in the Exome data base

| Variant Position | Allelles Non-Coding Strand Bases | Allele Present on Coding Strand syn-MUT | All Allele # | MAF (%) | GVS Function | Amino Acid | Protein Pos. | cDNA Pos. |
|---|---|---|---|---|---|---|---|---|
| 6:49403282 | C/T | G | C = 7894/T = 5112 | 38.3256/41.2165/39.3049 | missense | VAL, ILE | 671/751 | 2011 |
| 6:49403268 | G/A | A | G = 1/A = 13005 | 0.0116/0.0/0.0077 | coding-synonymous | none | 675/751 | 2025 |
| 6:49403270 | T/C | G | T = 1/C = 13005 | 0.0/0.0227/0.0077 | missense | THR, ALA | 675/751 | 2023 |
| 6:49403267 | T/C | G | T = 1/C = 13005 | 0.0/0.0227/0.0077 | missense | THR, ALA | 676/751 | 2026 |
| 6:49403260 | C/T | A | C = 1/T = 13005 | 0.0/0.0227/0.0077 | missense | ARG, HIS | 678/751 | 2033 |
| 6:49403194 | T/A | T | T = 1/A = 13005 | 0.0116/0.0/0.0077 | missense | LYS, MET | 700/751 | 2099 |
| 6:49399544 | A/C | G | A = 3/C = 13003 | 0.0/0.0681/0.0231 | missense | VAL, GLY | 717/751 | 2150 |
| 6:49399498 | A/G | A | A = 1/G = 13005 | 0.0116/0.0/0.0077 | coding-synonymous | none | 732/751 | 2196 |
| 6:49399476 | T/C | G | T = 1/C = 13005 | 0.0116/0.0/0.0077 | missense | LYS, GLU | 740/751 | 2218 |

In another aspect, SEQ ID NO:3, SEQ ID NO:4, SEQ ID NO:5, and SEQ ID NO:6 encodes a MUT protein that has 100% identity with the naturally occurring human MUT protein, or that has at least 90% amino acid identity to the naturally occurring human MUT protein. In a preferred embodiment, the polynucleotide encodes MUT protein that has at least 95% amino acid identity to naturally occurring human MUT protein.

In one embodiment, a polypeptide according to the invention retains at least 90% of the naturally occurring human MUT protein function, i.e., the capacity to catalyze the conversion of L-methylmalonyl-CoA to succinyl-CoA. In another embodiment, the encoded MUT protein retains at least 95% of the naturally occurring human MUT protein function. This protein function can be measured, for example, via the efficacy to rescue a neonatal lethal phenotype in Mut knock-out mice (Chandler, et al. 2010 *Mol Ther* 18:11-6) (FIG. 9), the lowering of circulating metabolites including methylmalonic acid in a disease model of MMA (Chandler, et al. 2010 *Mol Ther* 18:11-6; Carrillo-Carrasco, et al. 2010 *Hu Gene Ther* 21:1147-54; Senac, et al. 2012 *Gene Ther* 19:385-91) (FIG. 10), the measurement of whole body (Chandler, et al. 2010 *Mol Ther* 18:11-6; Senac, et al. 2012 *Gene Ther* 19:385-91) or hepatic $^1$-C-$^{13}$propionate oxidative capacity (Carrillo-Carrasco, et al. 2010 *Hu Gene Ther* 21:1147-54), or the correction of macromolecular $^1$-C-$^{14}$propionate incorporation in cell culture (Chandler, et al. 2007 *BMC Med Genet* 8:64).

In some embodiments, the synthetic polynucleotide exhibits at least equivalent and/or improved expression relative to the expression of naturally occurring human methylmalonyl-CoA mutase polynucleotide sequence. The improved expression can be due to the polynucleotide comprising codons that have been optimized relative to the naturally occurring human methylmalonyl-CoA mutase polynucleotide sequence. In one aspect, the synthetic polynucleotide has at least about 25%, at least about 30%, at least about 35%, at least about 40%, at least about 45%, at least about 50%, at least about 55%, at least about 60%, at least about 65%, at least about 70%, at least about 75%, at least about 80% of less commonly used codons replaced with more commonly used codons. In additional embodiments, the polynucleotide has at least 85%, 90%, or 95% replacement of less commonly used codons with more commonly used codons, and demonstrate equivalent or enhanced expression of MUT as compared to SEQ ID NO:3

In another embodiment, the synthetic polynucleotide of the invention exhibits therapeutically useful expression in a subject. The expression level of the MUT polypeptide is optionally at a level that provides for a clinically observable level of MUT activity in a subject. In some embodiments, the synthetic polynucleotide sequences of the invention preferably encode a polypeptide that retains at least about 80% of the enhanced MUT expression (as demonstrated by expression of the polynucleotide of SEQ ID NO:1, SEQ ID NO:4, SEQ ID NO:5, or SEQ ID NO:6 in an appropriate host, for example.) In additional embodiments, the polypeptide retains at least 85%, 90%, or 95% or 100% of the enhanced expression observed with the polynucleotide of SEQ ID NO:1, SEQ ID NO:4, SEQ ID NO:5, or SEQ ID NO:6.

In designing the synMUT of the present invention, the following considerations were balanced. For example, the fewer changes that are made to the nucleotide sequence of SEQ ID NO:3, decreases the potential of altering the secondary structure of the sequence, which can have a significant impact on gene expression. The introduction of undesirable restriction sites is also reduced, facilitating the subcloning of MUT into the plasmid expression vector. However, a greater number of changes to the nucleotide sequence of SEQ ID NO:3 allows for more convenient identification of the translated and expressed message, e.g. mRNA, in vivo. Additionally, greater number of changes to the nucleotide sequence of SEQ ID NO:3 provides for increased likelihood of greater expression. These considerations were balanced when arriving at SEQ ID NO:1, SEQ ID NO:4, SEQ ID NO:5, and/or SEQ ID NO:6. The polynucleotide sequences encoding synMUT allow for equivalent and/or increased expression of the synMUT gene(s) relative to naturally occurring human MUT sequences, or clinically observable expression. They are also engineered to have increased transcriptional, translational, and protein refolding efficacy. This engineering is accomplished by using human codon biases, evaluating GC, CpG, and negative GpC content, optimizing the interaction between the codon and anti-codon, and eliminating cryptic splicing sites and RNA instability motifs. Because the sequences are novel, they facilitate detection using nucleic acid-based assays.

MUT has a total of 750 amino acids and synMUT contains approximately 750 codons corresponding to said amino acids. Of these codons, in SEQ ID NO:1, approximately 463 codons are changed from that of the natural human MUT, however, as described, SEQ ID NO:1, despite changes from SEQ ID NO:3, codes for the amino acid sequence SEQ ID NO:2 for MUT. Codons for SEQ ID NO:1 are changed, in accordance with the equivalent amino acid positions of SEQ ID NO:2, at positions 2, 4, 5, 6, 8, 9, 10, 11, 12, 13, 14, 15, 17, 18, 19, 22, 23, 24, 25, 26, 27, 29, 30, 31, 32, 33, 36, 38, 39, 40, 41, 42, 44, 45, 47, 48, 49, 52, 59, 60, 63, 64, 65, 67, 68, 69, 70, 72, 73, 74, 75, 76, 77, 80, 81, 82, 83, 85, 90, 92, 93, 95, 96, 97, 98, 100, 103, 106, 107, 108, 110, 111, 112, 113, 117, 119, 120, 122, 128, 129, 130, 134, 135, 136, 137, 138, 141, 134, 147, 149, 150, 151, 152, 153, 154, 155, 156, 157, 160, 162, 164, 166, 170, 171, 173, 174, 177, 179, 180, 183, 184, 185, 187, 189, 190, 191, 192, 194, 195, 196, 198, 199, 200, 201, 203, 204, 206, 207, 208, 210, 211, 212, 213, 214, 215, 216, 217, 218, 219, 220, 221, 222, 224, 225, 227, 228, 230, 234, 235, 241, 243, 244, 245, 246, 247, 248, 249, 250, 254, 255, 256, 257, 220, 262, 263, 264, 270, 271, 272, 273, 278, 279, 280, 281, 284, 285, 286, 287, 289, 290, 292, 294, 298, 299, 300, 301, 302, 303, 304, 305, 306, 308, 312, 314, 315, 316, 318, 319, 320, 323, 325, 326, 328, 330, 332, 333, 335, 337, 342, 343, 344, 345, 346, 347, 348, 349, 350, 351, 352, 355, 357, 358, 360, 362, 363, 364, 365, 369, 370, 372, 373, 377, 378, 379, 381, 382, 384, 385, 388, 389, 392, 393, 394, 395, 396, 397, 398, 400, 401, 403, 405, 406, 407, 409, 411, 412, 413, 414, 416, 417, 418, 419, 420, 422, 424, 427, 432, 433, 434, 436, 437, 438, 432, 434, 435, 439, 450, 453, 456, 457, 458, 459, 462, 463, 464, 466, 467, 468, 469, 472, 473, 474, 475, 476, 477, 478, 479, 480, 481, 482, 483, 485, 486, 487, 488, 489, 494, 495, 499, 500, 502, 504, 505, 507, 508, 509, 511, 512, 513, 516, 517, 518, 520, 523, 524, 525, 527, 528, 529, 530, 532, 533, 534, 535, 536, 537, 538, 539, 542, 544, 545, 547, 548, 551, 553, 555, 556, 558, 560, 561, 563, 566, 567, 570, 571, 572, 573, 574, 575, 576, 577, 578, 581, 584, 585, 586, 588, 590, 591, 592, 594, 597, 598, 599, 600 604, 605, 606, 609, 610, 612, 613, 614, 615, 616, 617, 618, 619, 621, 624, 625, 626, 628, 629, 633, 635, 636, 637, 638, 640, 641, 642, 644, 646, 627, 630, 633, 634, 635, 636, 637, 638, 661, 662, 663, 664, 667, 668, 669, 670, 671, 672, 673, 674, 675, 677, 679, 681, 682, 683, 686, 689, 691, 692, 693, 694, 696, 697, 698, 701, 702, 703, 705, 707, 710, 711, 714, 715, 716, 717, 718, 719, 720, 721, 722, 723, 724, 725, 726, 727, 728, 729, 731, 732, 733, 734, 735, 736, 740, 743, 745, 746, 748, 749, 750 of SEQ ID NO:2, relative to the natural human sequence SEQ ID NO:3. In this embodiment, the amino acid sequence for natural human MUT has been retained.

It can be appreciated that partial reversion of the designed synMUT molecules disclosed herein (SEQ ID NO:1, SEQ ID NO:4, SEQ ID NO:5, and/or SEQ ID NO:6) to codons that are found in MUT can be expected to result in nucleic acid sequences that, when incorporated into appropriate vectors, can also exhibit the desirable properties of SEQ ID NO:1, SEQ ID NO:4, SEQ ID NO:5, and/or SEQ ID NO:6, for example, such partial reversion variants can have at least equivalent expression of MUT and/or clinically useful or observable expression from a vector inserted into an appropriate host, as SEQ ID NO:1, SEQ ID NO:4, SEQ ID NO:5, and/or SEQ ID NO:6. For example, the invention includes nucleic acids in which at least about 1 altered codon, at least about 2 altered codons, at least about 3, altered codons, at least about 4 altered codons, at least about 5 altered codons, at least about 6 altered codons, at least about 7 altered codons, at least about 8 altered codons, at least about 9 altered codons, at least about 10 altered codons, at least about 11 altered codons, at least about 12 altered codons, at least about 13 altered codons, at least about 14 altered codons, at least about 15 altered codons, at least about 16 altered codons, at least about 17 altered codons, at least about 18 altered codons, at least about 20 altered codons, at least about 25 altered codons, at least about 30 altered codons, at least about 35 altered codons, at least about 40 altered codons, at least about 50 altered codons, at least about 55 altered codons, at least about 60 altered codons, at least about 65 altered codons, at least about 70 altered codons, at least about 75 altered codons, at least about 80 altered codons, at least about 85 altered codons, at least about 90 altered codons, at least about 95 altered codons, at least about 100 altered codons, at least about 110 altered codons, at least about 120 altered codons, at least about 130 altered codons, at least about 130 altered codons, at least about 140 altered codons, at least about 150 altered codons, at least about 160 altered codons, at least about 170 altered codons, at least about 180 altered codons, at least about 190 altered codons, at least about 200 altered codons, at least about 220 altered codons, at least about 240 altered codons, at least about 260 altered codons, at least about 280 altered codons, at least about 300 altered codons, at least about 320 altered codons, at least about 340 altered codons, at least about 360 altered codons, at least about 380 altered codons, at least about 400 altered codons, at least about 420 altered codons, at least about 440 altered codons, at least about 460 altered codons, or at least about 480 of the altered codon positions in SEQ ID NO:1, SEQ ID NO:4, SEQ ID NO:5, and/or SEQ ID NO:6 are reverted to native codons according to SEQ ID NO:3, an alternate codon sequence for an amino acid sequence as shown in FIG. 1, or to SEQ ID NO:3 containing SNPs (alleles) as noted in Table 1, and having at least equivalent expression to SEQ ID NO:1, SEQ ID NO:4, SEQ ID NO:5, and/or SEQ ID NO:6. Alternately, at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the altered codon positions in SEQ ID NO:1, SEQ ID NO:4, SEQ ID NO:5, and/or SEQ ID NO:6 are reverted to native sequence according to SEQ ID NO:3, an alternate codon sequence for an amino acid sequence as shown in FIG. 1, or to SEQ ID NO:3 containing SNPs as noted in Table 1, and having at least equivalent expression to SEQ ID NO:3. In other embodiments, polynucleotides of the invention have expression in a subject or host of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the expression of SEQ ID NO:1, SEQ ID NO:4, SEQ ID NO:5, and/or SEQ ID NO:6.

In some embodiments, polynucleotides of the present invention do not share 100% identity with SEQ ID NO:3. In other words, in some embodiments, polynucleotides having 100% identity with SEQ ID NO:3 are excluded from the embodiments of the present invention.

The synthetic polynucleotide can be composed of DNA and/or RNA or a modified nucleic acid, such as a peptide nucleic acid, and could be conjugated for improved biological properties.

Therapy

In another aspect, the invention comprises a method of treating a disease or condition mediated by methylmalonyl-CoA mutase. The disease or condition can, in one embodiment, be methylmalonic acidemia (MMA). This method comprises administering to a subject in need thereof a synthetic methylmalonyl-CoA mutase polynucleotide construct comprising the synthetic polynucleotides (synMUT) (e.g., SEQ ID NO:1, SEQ ID NO:4, SEQ ID NO:5, and/or SEQ ID NO:6) described herein. The MUT enzyme is processed after transcription, translation, and translocation into the mitochondrial inner space. During this importation and maturation process, amino acids 1-32 are removed to produce the mature MUT peptide, comprised of residues 33-750. Thus, in another embodiment, the invention includes the portion of the synMUT enzyme located inside the mitochondrial matrix, specifically, residues 33-750 corresponding to nucleotides 62-2250 of a nucleotide of the present invention, e.g., SEQ ID NO:1, SEQ ID NO:4, SEQ ID NO:5, and/or SEQ ID NO:6, e.g. synMUT1-4, attached to a carrier, synthetic or heterologous mitochondrial leader sequence, charged or lipophilic small molecule to direct toward the mitochondria; conjugated or covalently modified to a peptide that targets the mitochondrial matrix; or encapsulated to deliver this fragment of synMUT to a subcellular organelle, cell type or tissue.

Enzyme replacement therapy consists of administration of the functional enzyme (methylmalonyl-CoA mutase) to a subject in a manner so that the enzyme administered will catalyze the reactions in the body that the subject's own defective or deleted enzyme cannot. In enzyme therapy, the defective enzyme can be replaced in vivo or repaired in vitro using the synthetic polynucleotide according to the invention. The functional enzyme molecule can be isolated or produced in vitro, for example. Methods for producing recombinant enzymes in vitro are known in the art. In vitro enzyme expression systems include, without limitation, cell-based systems (bacterial (for example, *Escherichia coli, Corynebacterium, Pseudomonas fluorescens*), yeast (for example, *Saccharomyces cerevisiae, Pichia pastoris*), insect cell (for example, Baculovirus-infected insect cells, non-lytic insect cell expression), and eukaryotic systems (for example, *Leishmania*)) and cell-free systems (using purified RNA polymerase, ribosomes, tRNA, ribonucleotides). Viral in vitro expression systems are likewise known in the art. The enzyme isolated or produced according to the above-iterated methods exhibits, in specific embodiments, 80%, 85%, 90%, 95%, 98%, 99%, or 100% homology to the naturally occurring (for example, human) methylmalonyl-CoA mutase.

Gene therapy can involve in vivo gene therapy (direct introduction of the genetic material into the cell or body) or ex vivo gene transfer, which usually involves genetically altering cells prior to administration. In one aspect, genome editing, or genome editing with engineered nucleases (GEEN) may be performed with the synMUT nucleotides of the present invention allowing synMUT DNA to be inserted, replaced, or removed from a genome using artificially engineered nucleases. Any known engineered nuclease may be used such as Zinc finger nucleases (ZFNs), Transcription Activator-Like Effector Nucleases (TALENs), the CRISPR/Cas system, and engineered meganuclease re-engineered homing endonucleases. Alternately, the nucleotides of the present invention including synMUT, in combination with a CASP/CRISPR, ZFN, or TALEN can be used to engineer correction at the locus in a patient's cell either in vivo or ex vivo, then, in one embodiment, use that corrected cell, such as a fibroblast or lymphoblast, to create an iPS or other stem cell for use in cellular therapy.

Administration/Delivery and Dosage Forms

Routes of delivery of a synthetic methylmalonyl-Co-A mutase (MUT) polynucleotide according to the invention may include, without limitation, injection (systemic or at target site), for example, intradermal, subcutaneous, intravenous, intraperitoneal, intraocular, subretinal, renal artery, hepatic vein, intramuscular injection; physical, including ultrasound(-mediated transfection), electric field-induced molecular vibration, electroporation, transfection using laser irradiation, photochemical transfection, gene gun (particle bombardment); parenteral and oral (including inhalation aerosols and the like). Related methods include using genetically modified cells, antisense therapy, and RNA interference.

Vehicles for delivery of a synthetic methylmalonyl-CoA mutase polynucleotide (e.g., synMUT1-4) according to the invention may include, without limitation, viral vectors (for example, AAV, adenovirus, baculovirus, retrovirus, lentivirus, foamy virus, herpes virus, Moloney murine leukemia virus, Vaccinia virus, and hepatitis virus) and non-viral vectors (for example, naked DNA, mini-circles, liposomes, ligand-polylysine-DNA complexes, nanoparticles, cationic polymers, including polycationic polymers such as dendrimers, synthetic peptide complexes, artificial chromosomes, and polydispersed polymers). Thus, dosage forms contemplated include injectables, aerosolized particles, capsules, and other oral dosage forms.

In certain embodiments, the vector used for gene therapy comprises an expression cassette. The expression cassette may, for example, consist of a promoter, the synthetic polynucleotide, and a polyadenylation signal. Viral promoters include, for example, the ubiquitous cytomegalovirus immediate early (CMV-IE) promoter, the chicken beta-actin (CBA) promoter, the simian virus 40 (SV40) promoter, the Rous sarcoma virus long terminal repeat (RSV-LTR) promoter, the Moloney murine leukemia virus (MoMLV) LTR promoter, and other retroviral LTR promoters. The promoters may vary with the type of viral vector used and are well-known in the art.

In one specific embodiment, synMUT could be placed under the transcriptional control of a ubiquitous or tissue-specific promoter, with a 5' intron, polyadenylation signal, and mRNA stability element, such as the woodchuck post-transcriptional regulatory element. The use of a tissue-specific promoter can restrict unwanted transgene expression, as well as facilitate persistent transgene expression. The therapeutic transgene could then be delivered as coated or naked DNA into the systemic circulation, portal vein, or directly injected into a tissue or organ, such as the liver or kidney. In addition to the liver or kidney, the brain, pancreas, eye, heart, lungs, bone marrow, and muscle may constitute targets for therapy. Other tissues or organs may be additionally contemplated as targets for therapy.

In another embodiment, the same synMUT expression construct could be packaged into a viral vector, such as an adenoviral vector, retroviral vector, lentiviral vector, or adeno-associated viral vector, and delivered by various means into the systemic circulation, portal vein, or directly injected into a tissue or organ, such as the liver or kidney. In addition to the liver or kidney, the brain, pancreas, eye, heart, lungs, bone marrow, and muscle may constitute targets for therapy. Other tissues or organs may be additionally contemplated as targets for therapy.

Tissue-specific promoters include, without limitation, Apo A-I, ApoE, hAAT, transthyretin, liver-enriched activator, albumin, PEPCK, and $RNAP_{II}$ promoters (liver), PAI-1, ICAM-2 (endothelium), MCK, SMC α-actin, myosin heavy-chain, and myosin light-chain promoters (muscle), cytokeratin 18, CFTR (epithelium), GFAP, NSE, Synapsin I, Preproenkephalin, dβH, prolactin, and myelin basic protein promoters (neuronal), and ankyrin, α-spectrin, globin, HLA-DRα, CD4, glucose 6-phosphatase, and dectin-2 promoters (erythroid).

Regulable promoters (for example, ligand-inducible or stimulus-inducible promoters) are also contemplated for expression constructs according to the invention.

In yet another embodiment, synMUT could be used in ex vivo applications via packaging into a retro- or lentiviral vector to create an integrating vector that could be used to permanently correct any cell type from a patient with MUT deficiency. The synMUT-transduced and corrected cells could then be used as a cellular therapy. Examples might include CD34+ stem cells, primary hepatocytes, or fibroblasts derived from patients with MUT deficiency. Fibroblasts could be reprogrammed to other cell types using iPS methods well known to practitioners of the art. In yet another embodiment, synMUT could be recombined using genomic engineering techniques that are well known to practitioners of the art, such as ZFNs and TALENS, into the MUT locus, a genomic safe harbor site, such as AAVS1, or into another advantageous location, such as into rDNA, the albumin locus, GAPDH, or a suitable expressed pseudogene.

A composition (pharmaceutical composition) for treating an individual by gene therapy may comprise a therapeutically effective amount of a vector comprising the synMUT transgenes or a viral particle produced by or obtained from same. The pharmaceutical composition may be for human or animal usage. Typically, a physician will determine the actual dosage which will be most suitable for an individual subject, and it will vary with the age, weight, and response of the particular individual.

The composition may, in specific embodiments, comprise a pharmaceutically acceptable carrier, diluent, excipient, or adjuvant. Such materials should be non-toxic and should not interfere with the efficacy of the transgene. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences [Mack Pub. Co., 18th Edition, Easton, Pa. (1990)]. The choice of pharmaceutical carrier, excipient, or diluent can be selected with regard to the intended route of administration and standard pharmaceutical practice. The pharmaceutical compositions may comprise as, or in addition to, the carrier, excipient, or diluent any suitable binder(s), lubricant(s), suspending agent(s), coating agent(s), solubilizing agent(s), and other carrier agents that may aid or increase the viral entry into the target site (such as for example a lipid delivery system). For oral administration, excipients such as starch or lactose may be used. Flavoring or coloring agents may be included, as well. For parenteral administration, a sterile aqueous solution may be used, optionally containing other substances, such as salts or monosaccharides to make the solution isotonic with blood.

A composition according to the invention may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, modulators, or drugs (e.g., antibiotics).

The composition may be in a variety of forms. These include, for example, liquid, semi-solid and solid dosage forms, such as liquid solutions (e.g., injectable and infusible solutions), dispersions or suspensions, tablets, pills, powders, liposomes and suppositories. Additional dosage forms contemplated include: in the form of a suppository or pessary; in the form of a lotion, solution, cream, ointment or dusting powder; by use of a skin patch; in capsules or ovules; in the form of elixirs, solutions, or suspensions; in the form of tablets or lozenges.

EXAMPLES

Cell Culture Studies

A synthetic codon-optimized human methylmalonyl-Co-A mutase gene (synMUT) was engineered using an iterative approach, wherein the naturally occurring MUT cDNA (NCBI Reference Sequence: NM_000255.3) was optimized codon by codon to create synMUT (FIG. 2) using OptimumGene™ codon optimization software (Genscript Inc) that incorporates critical factors involved in protein expression, such as codon adaptability, mRNA structure, and various cis-elements in transcription and translation. The resulting sequence that was selected had the maximal divergence from the MUT cDNA at the nucleotide level yet retained optimally utilized codons at each position.

To improve the expression of methylmalonyl-CoA mutase and create a vector that could express the human MUT gene in a more efficient fashion, synMUT was cloned using restriction endonuclease excision and DNA ligation into an expression vector under the control of the chicken β-actin promoter (Chandler, et al. 2010 Mol Ther 18:11-6). The construct expressing either the full-length MUT or the full-length synMUT was then transfected into 293FT cells using Lipofectamine™ (Life Technologies). Cloning and transfection methods are well understood by practitioners of the art (Sambrook, Fritsch, Maniatis. Molecular Cloning: A Laboratory Manual). After 48 hours, cellular protein was extracted from the transfected cells and evaluated for methylmalonyl-CoA mutase protein expression using Western analysis (Chandler, et al. 2010 Mol Ther 18:11-6). The results show that synMUT is transcribed and translated as or more efficiently than MUT (FIG. 6). FIG. 6 shows expression of MUT protein following transfection of HEK-293 cells in vitro with synMUT. FIG. 6(A) shows schematic of the expression constructs prepared as described in Chandler, et al. 2010 Mol Ther 18:11-6. Figure (B) shows HEK-293 cells transfected with green fluorescent protein (GFP), human codon optimized methylmalonyl-CoA mutase (labeled CBA-synMUT) or human methylmalonyl-CoA mutase (labeled CBA-MUT) expression construct. Cells transfected with CBA-synMUT exhibited a significant increase in the expression of MUT in comparison to cells transfected with GFP or CBA-MUT.

Gene Therapy in Methylmalonyl-CoA Mutase Knock-Out (Mut$^{-/-}$) Mice.

The targeted Mut allele harbors a deletion of exon 3 in the Mut gene. This exon encodes the putative substrate-binding pocket in the Mut enzyme. The Mut allele does not produce mature RNA, protein, or enzymatic activity. Mut$^{-/-}$ mice (mice having the Mut gene knocked out (disrupted or replaced) on a mixed (C57BL/6×[129SV/Ev×FvBN]) background exhibit a semipenetrant neonatal lethal phenotype, with most mice perishing in the early neonatal period. In the instant example, the Mut$^{-/-}$ (methylmalonyl-CoA mutase knockout) mouse is also referred to as the mouse with MMA.

Mut$^{-/-}$ mice display massively elevated methylmalonic acid concentrations in the plasma that progressively rises to the 2 mmol/L range, until death occurs. Mut$^{+/-}$ animals have biochemical parameters identical to Mut$^{+/+}$ wild-type animals and were used as controls throughout. This animal model of MMA, therefore, recapitulates the severest form of the human condition—mut$^O$ methylmalonic acidemia.

The synMUT polynucleotide was then used to construct a series of novel gene therapy vectors to treat mice with MMA. One vector is designed to express synMUT in the liver of the MMA mouse and used to make a recombinant adeno-associated viral vector.

Figure 7:
FIG. 7 presents a map of the AAV-HCR-hAAT-synMUT construct.

The AAV2/8-HCR-hAAT-RBG vector contains transcriptional control elements from the hepatic control region (HCR) and human alpha antitrypsin promoter (hAAT), cloning sites for the insertion of a complementary DNA, and the rabbit β-globin polyadenylation (RBG) signal (FIG. 7). Terminal repeats from AAV serotype 2 flank the expression cassette. The human codon-optimized methylmalonyl-CoA mutase (synMUT) was cloned into AAV2-HCR-hAAT-RBG and packaged into rAAV8 as previously described (Chandler, et al. 2010 *Mol Ther* 18:11-6), purified by cesium chloride centrifugation, and titered by qPCR to make the AAV8-HCR-hAAT-synMUT-RBG vector as previously described (Chandler, et al. 2010 *Mol Ther* 18:11-6; Carrillo-Carrasco, et al. 2010 *Hum Gene Ther* 21:1147-54). Animal studies were reviewed and approved by the National Human Genome Research Institute Animal User Committee. Hepatic injections were performed on non-anesthetized neonatal mice, typically within several hours after birth. Viral particles were diluted to a total volume of 20 microliters with phosphate-buffered saline immediately before injection and were delivered into the liver parenchyma using a 32-gauge needle and transdermal approach, as previously described.

Figure 8:
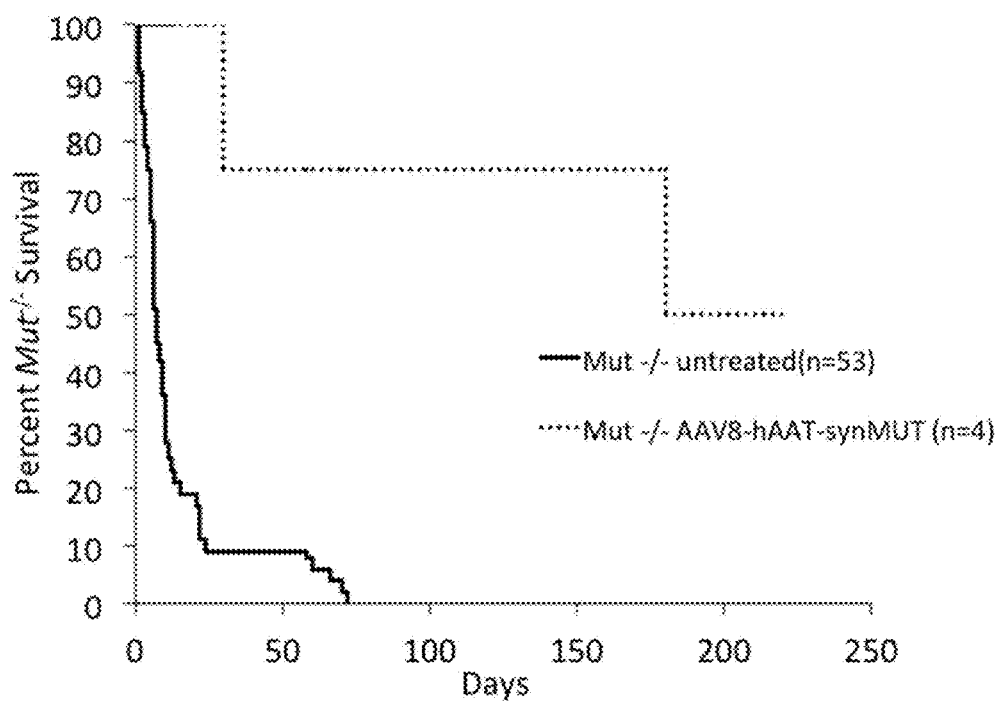
FIG. 8 illustrates the increased survival of Mut$^{-/-}$ mice after treatment with the AAV8-HCR-hAAT-synMUT construct.
Figure 9:
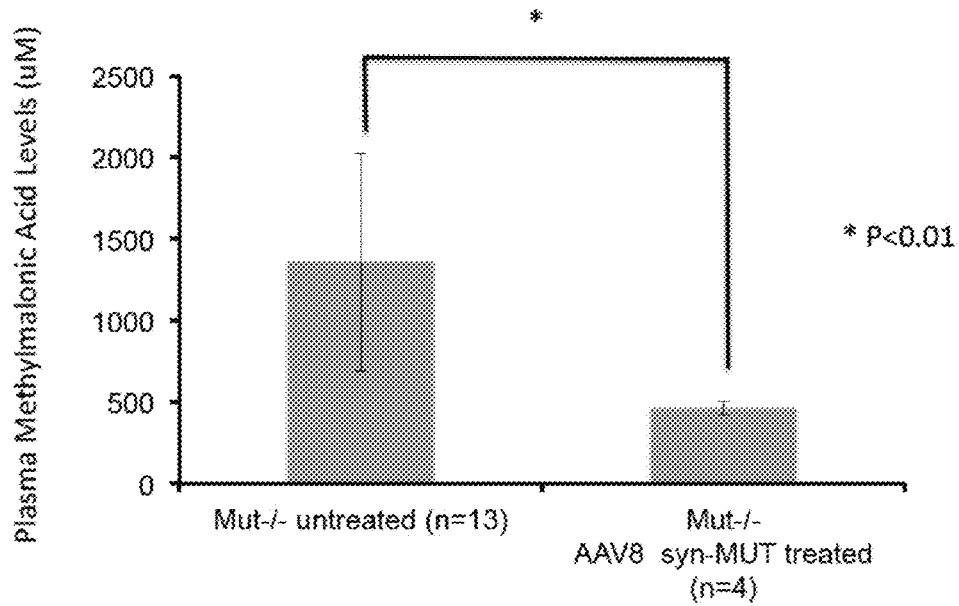
FIG. 9 illustrates the reduction in circulating metabolites in Mut$^{-/-}$ mice after treatment with the AAV8-HCR-hAAT-synMUT construct.

Treatment with synMUT polynucleotide delivered using an AAV (adeno-associated virus) rescued the Mut$^{-/-}$ mice from neonatal lethality (FIG. 8), improved their growth, and lowered the levels of plasma methylmalonic acid in the blood (FIG. 9). This establishes the pre-clinical efficacy of synMUT as a treatment for MMA in vivo, including in other animal models, as well as in humans. FIG. 8 shows increased survival of Mut$^{-/-}$ mice following treatment with AAV8-HCR-hAAT-synMUT. Mut$^{-/-}$ mice received a single intra-hepatic injection of 1×10$^{11}$ GC of AAV8-HCR-hAAT-synMUT at birth. All of the treated Mut$^{-/-}$ mice survived until day 30 and appeared normal relative to unaffected littermates. At day 30, a single treated Mut$^{-/-}$ mouse was sacrificed to evaluate the in vivo expression of MUT (see FIG. 9). FIG. 9 shows metabolic correction after AAV8-HCR-hAAT-synMUT gene therapy. A significant reduction in the plasma MMA levels on day of life 90 were documented in Mut$^{-/-}$ mice that received a single intra-hepatic injection of 1×10$^{11}$ GC of AAV8-HCR-hAAT-synMUT at birth.

Figure 10:
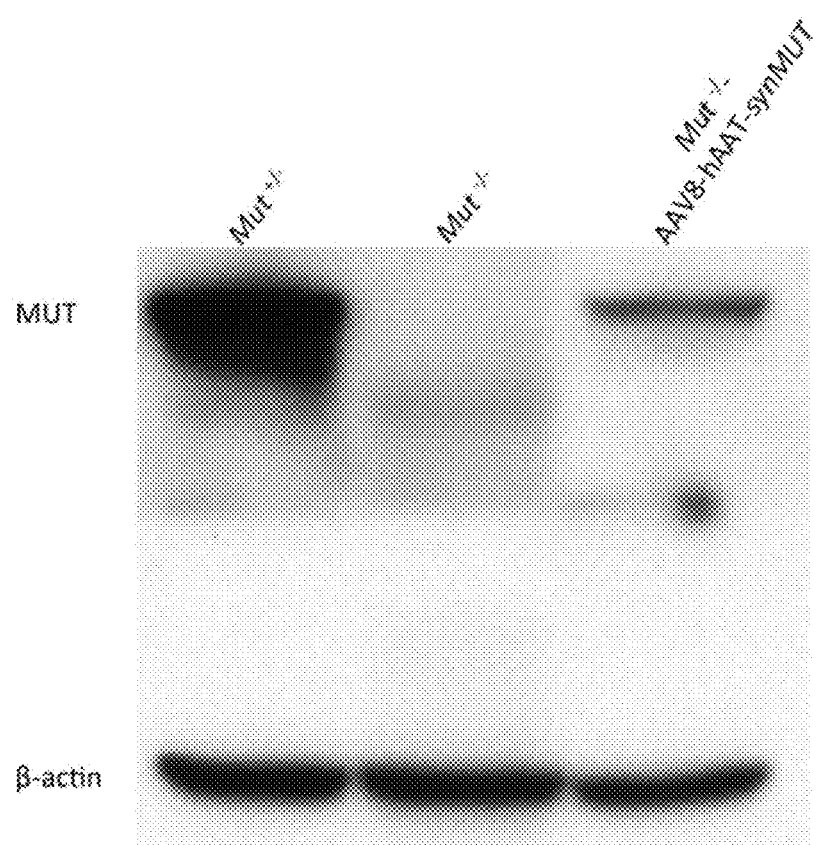
FIG. 10 shows expression of MUT in the liver after AAV8-HCR-hAAT-synMUT gene therapy.

A single treated Mut$^{-/-}$ mouse was sacrificed at 30 days after treatment with AAV2/8-HCR-hAAT-synMUT-RBG to evaluate in vivo expression of MUT (FIG. 10). FIG. 10 shows hepatic expression of MUT in a rescued Mut$^{-/-}$ mouse following treatment with AAV8-HCR-hAAT-synMUT. The liver of the treated Mut$^{-/-}$ mouse maintained a significant amount of MUT expression 30 days after treatment with AAV8-hAAT-synMUT, but less than that of untreated wild-type mice (Mut$^{+/-}$). By comparison, the liver of an untreated Mut$^{-/-}$ mouse exhibited no detectable MUT protein.

It was observed that the liver of the treated Mut$^{-/-}$ mouse demonstrated continued expression of MUT at 30 days after treatment with AAV2/8-HCR-hAAT-synMUT-RBG, but less than that of untreated wild-type mice (Mut$^{+/+}$). The untreated Mut$^{-/-}$ mouse exhibited no detectable MUT protein expression.

Safety Study in Mice.

Figure 11:
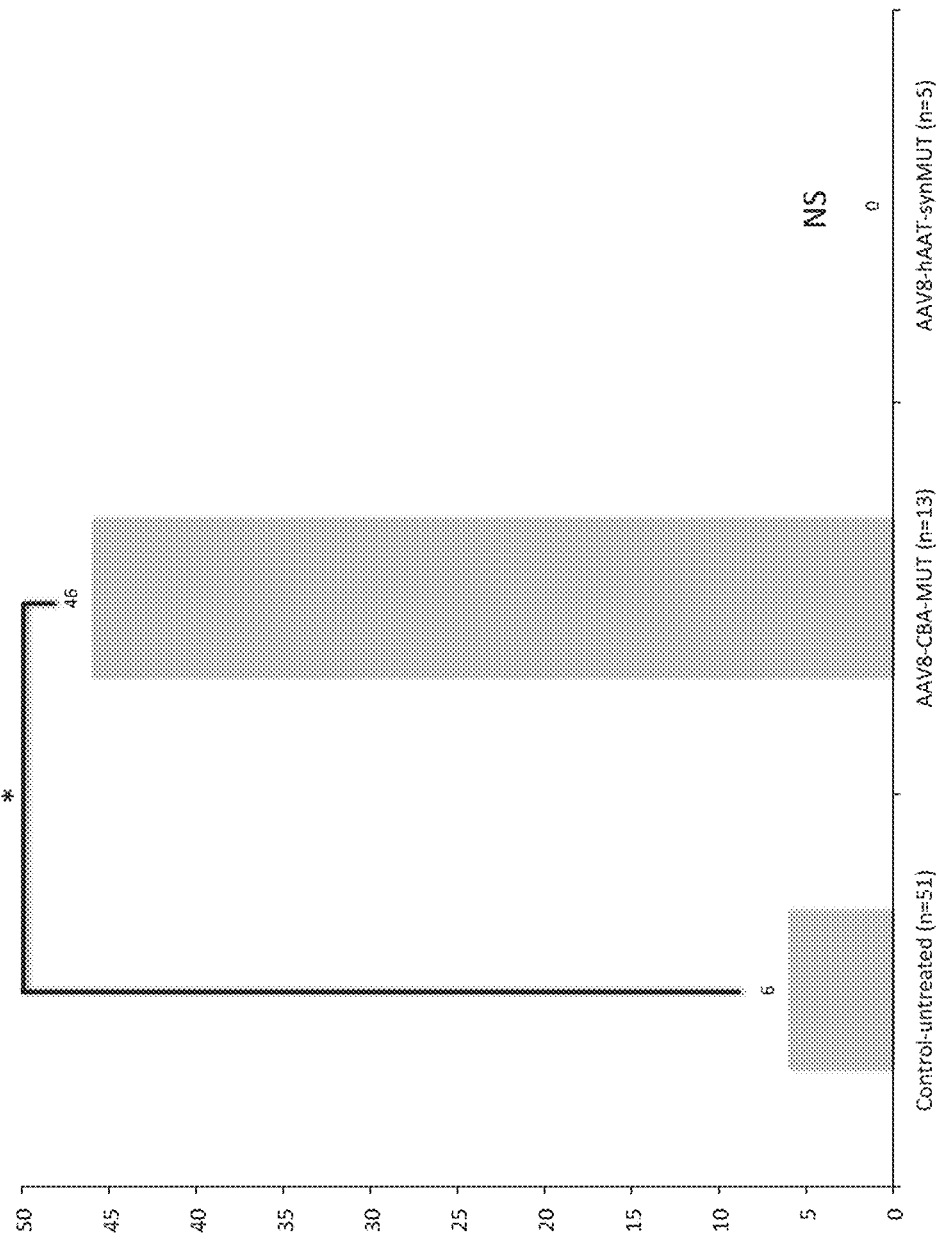
FIG. 11 shows an incidence of hepatocellular carcinoma following AAV Delivery-Mut+/− mice were either untreated (n=51), treated with 1-2×10$^{11}$ GC of AAV8-CBA-MUT (n=13) or 1-2×10$^{11}$ GC of AAV8-hAAT-synMUT (n=5) by intrahepatic injection at birth. *=P<0.01, NS=not statistically significant from untreated control group.

AAV genotoxicity, specifically hepatocarcinoma (HCC) in mice following AAV gene delivery, has been reported raising concerns about the safety of AAV gene therapy. We observed a similar increase in the occurrence of HCC following the treatment of mice with an AAV8-CBA-MUT we designed (FIG. 11). However, we do not observe any significant increase in the occurrence of HCC when mice are treated in a similar manner with AAV8-hAAT-synMUT. The data demonstrate that the AAV8-hAAT-synMUT is less genotoxic and has a better safety profile than that AAV8-CBA-MUT. These findings suggest that AAV8-hAAT-synMUT is a potentially safer AAV construct for human clinical trials.

Additional synMUT Sequences.

A number of additional synMUT nucleotides have been generated (SEQ ID NO:4, SEQ ID NO:5, and SEQ ID NO:6) according to the methods and principles disclosed hereinabove. These new alleles synMUT2-4 are new alleles synthesized using codon optimization. FIG. 12 shows a summary of the CLUSTAL W (1.83) multiple sequence alignment of wild type human MUT (hMUT)(SEQ ID NO:3) compared to synthetic, codon optimized MUT alleles (1-4)(SEQ ID NO:1, SEQ ID NO:4, SEQ ID NO:5, SEQ ID NO:6, respectively) depicted as percent identity to hMUT. As suggested by the alignment, there is substantial nucleotide divergence at the level of percent identity between all MUT alleles.

FIG. 13 shows a summary of the CLUSTAL W (1.83) multiple sequence alignment synthetic, codon optimized MUT alleles (synMUT1-4)(SEQ ID NO:1, SEQ ID NO:4, SEQ ID NO:5, SEQ ID NO:6, respectively) depicted as percent identity to synMUT1 (SEQ ID NO:1). As suggested by the alignment, there is substantial nucleotide divergence at the level of percent identity within the synMUT alleles.

Figure 14:
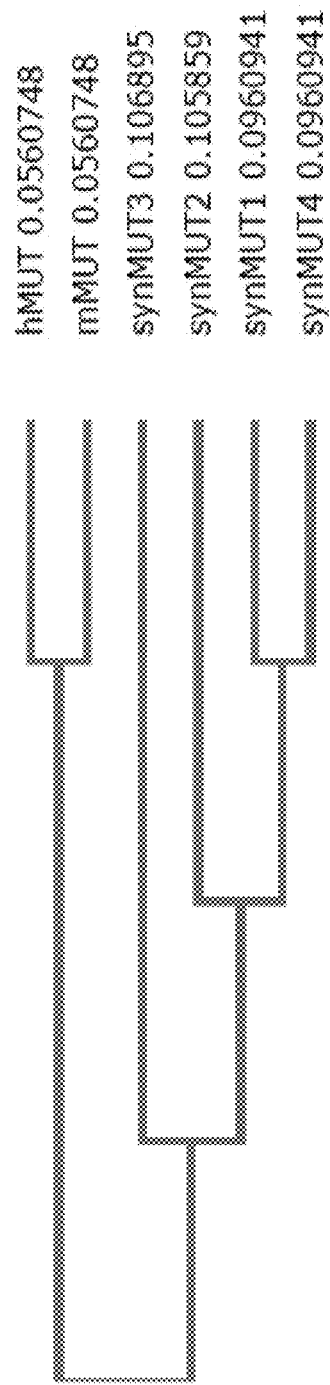
FIG. 14 shows a phylogenetic analysis of MUT alleles (SEQ ID NO:1, SEQ ID NO:4, SEQ ID NO:5, SEQ ID NO:6).
Figure 15:
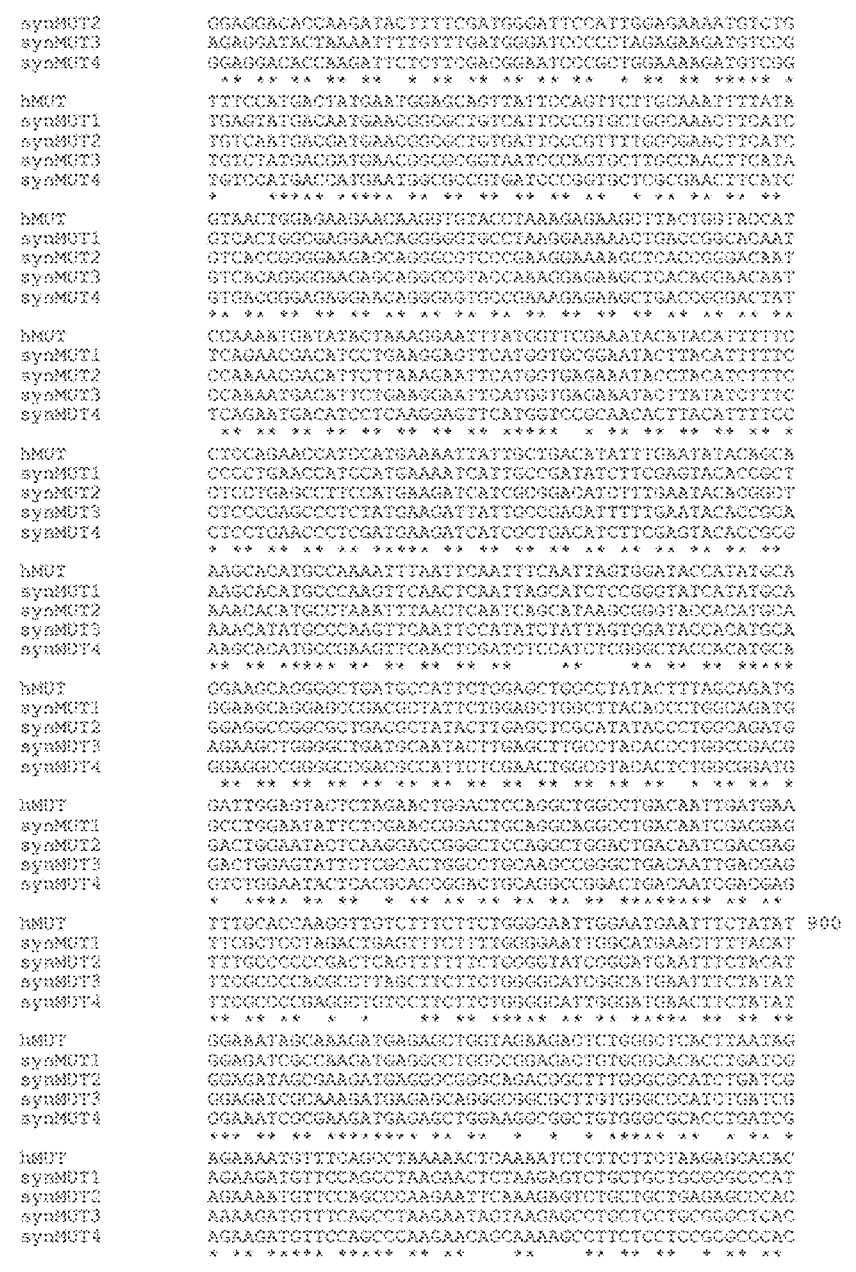
Figure 15:
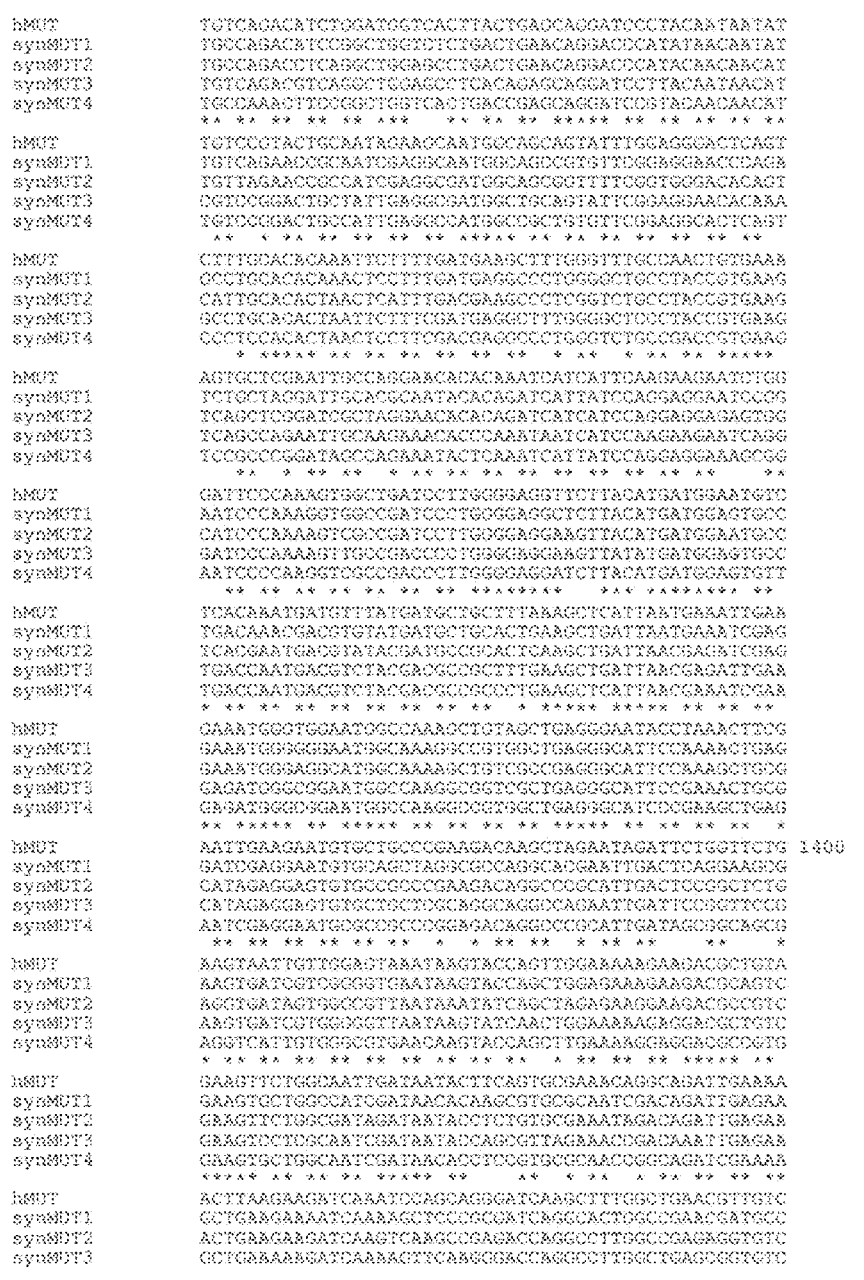
Figure 15:
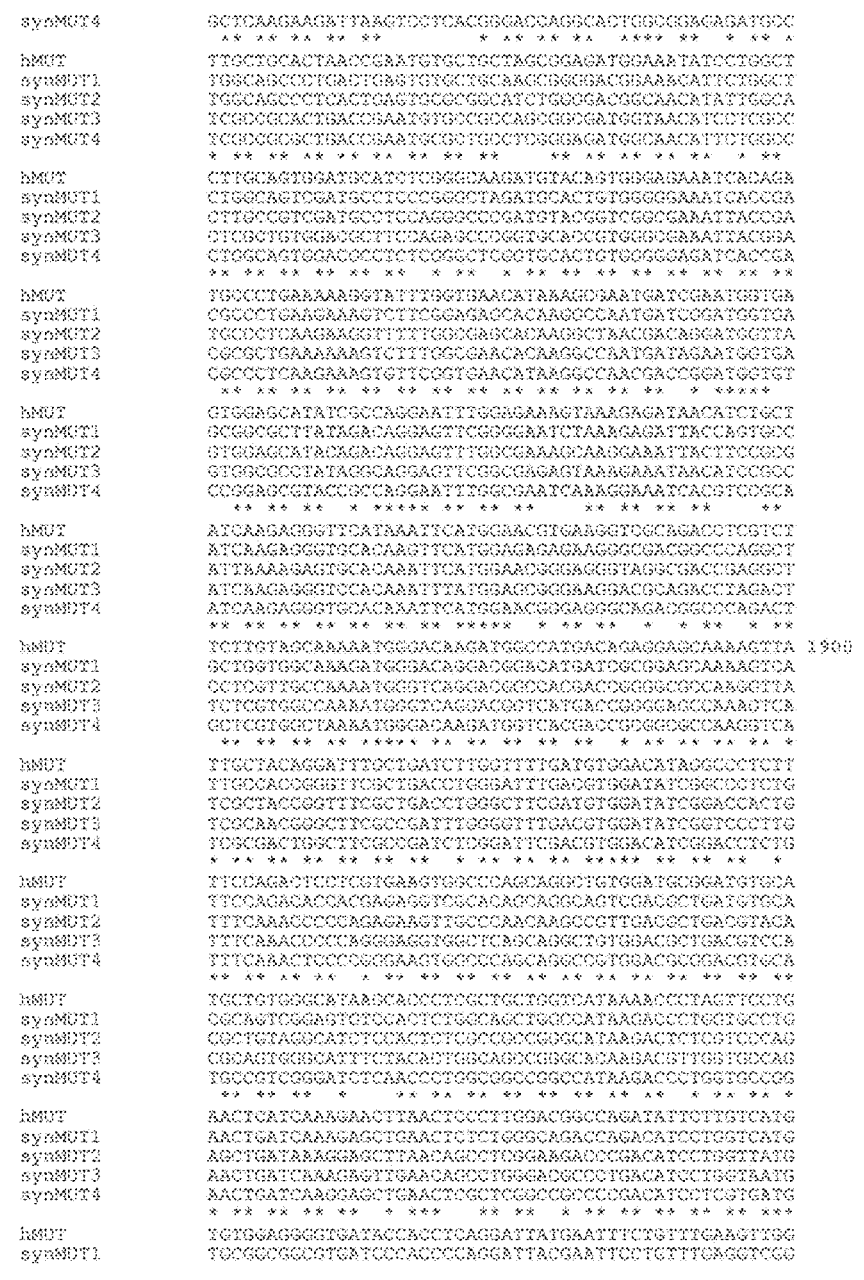
Figure 16:
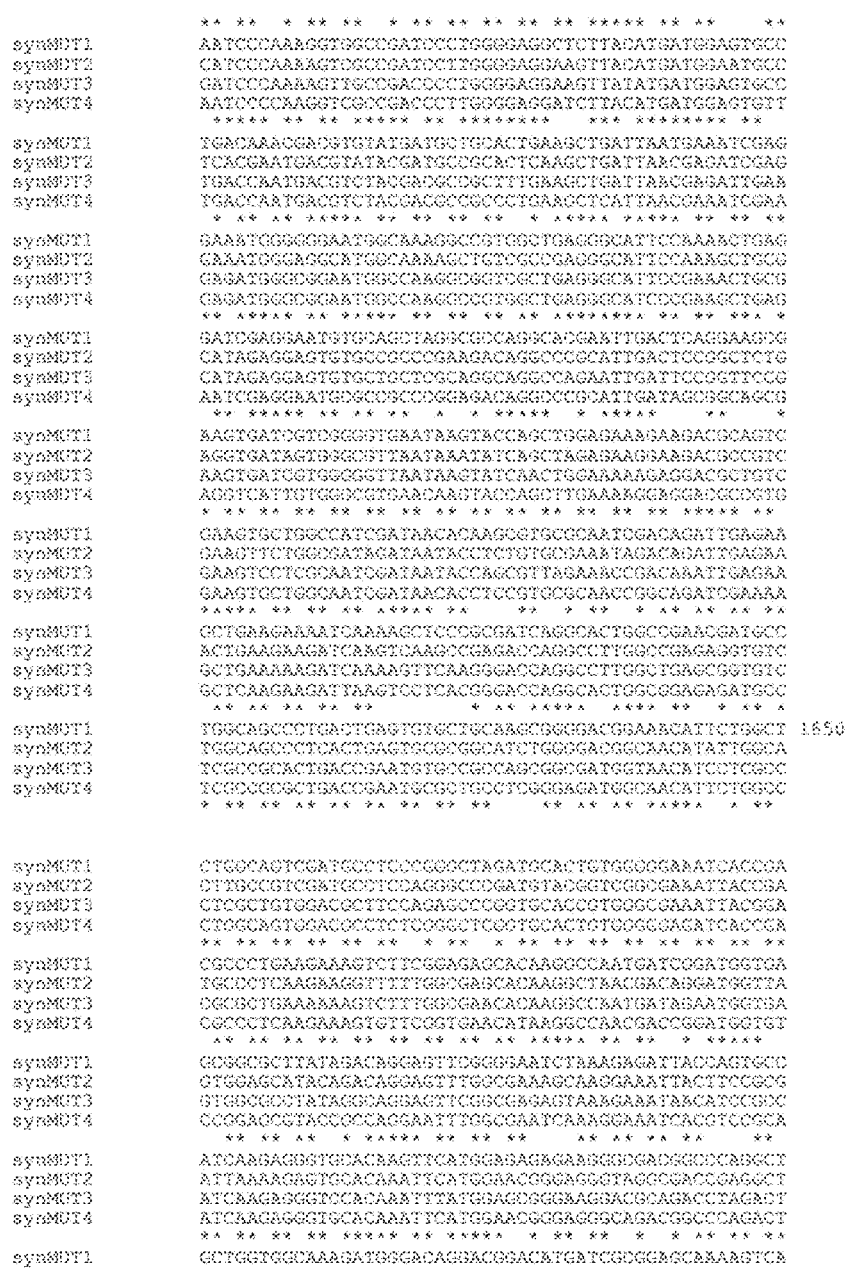

A CLUSTAL W alignment was used to construct a phylogenetic tree to depict the inferred relationship between the synthetic MUT alleles compared to wild type mouse (mMUT) and human (hMUT) sequences. As can be easily appreciated, the human and mouse wild type alleles appear more related to each other than to any of the codon optimized human MUT alleles. Within the synMUT group, each allele appears distinct with synMUT1 and synMUT4 grouping together despite sequence differences as large as between synMUT1 and synMUT2 or synMUT3. FIG. 14 shows the phylogenetic analysis of MUT alleles (SEQ ID NO:1, SEQ ID NO:4, SEQ ID NO:5, SEQ ID NO:6). FIG. 15 shows CLUSTAL W (1.83) multiple sequence alignment of wild type human MUT (hMUT) (SEQ ID NO:3) compared to synthetic, codon optimized MUT alleles (synMUT1-4)(SEQ ID NO:1, SEQ ID NO:4, SEQ ID NO:5, SEQ ID NO:6). An asterisk indicates a conserved base, with the numbering beginning at the first base pair of the coding sequence. Note the significant divergence of the synMUT alleles from the wild type hMUT. FIG. 16 shows CLUSTAL W (1.83) multiple sequence alignment of synthetic, codon optimized MUT alleles (synMUT1-4)(SEQ ID NO:1, SEQ ID NO:4, SEQ ID NO:5, SEQ ID NO:6). An asterisk indicates a conserved base, with the numbering beginning at the first base pair of the coding sequence.

Each MUT allele was cloned into an AAV vector under the control of the enhanced chicken beta actin (CBA) promoter. 293T cells were transfected with 5 μg of the DNA vector and expression of the varied MUT transgenes was studied by Western blotting. FIG. 17 shows the Western blot analysis of MUT expression in 293T cells. Actin served as a control. 20 μg of cell lysate was subjected to Western analysis and probed with an anti-MUT antibody or anti-actin antibody. The intensity of the control to the MUT band was calculated and compared to WT hMUT. The synMUT4 allele achieved at least 1.4 fold increased expression compared to the wild type human MUT gene, and more than any other synMUT allele. Repeat studies, conducted 3 times, have yielded 1.4-1.7-fold increased expression of synMUT4 compared to WT hMUT, WT mouse MUT or other codon-optimized synMUT alleles. The DNA sequences of each AAV are not shown. The synMUT alleles of the invention represent a series of new gene therapy vectors for MUT MMA.

The invention claimed is:

1. A synthetic methylmalonyl-CoA mutase (MUT) polynucleotide (synMUT) selected from the group consisting of:
   a) a polynucleotide comprising a nucleic acid sequence selected from the group consisting of: SEQ ID NO:1, SEQ ID NO:4, SEQ ID NO:5, and SEQ ID NO:6;
   b) a polynucleotide comprising a polynucleotide having a nucleic acid sequence with at least about 80% identity to the nucleic acid sequence of SEQ ID NO:1, SEQ ID NO:4, SEQ ID NO:5, or SEQ ID NO:6, and encoding a polypeptide having 100% identity to SEQ ID NO:2, and is capable of having at least equivalent expression in a host to SEQ ID NO:1, SEQ ID NO:3, SEQ ID NO:4, SEQ ID NO:5, or SEQ ID NO:6 expression, wherein the polynucleotide of a) or b) does not have the nucleic acid sequence of SEQ ID NO:3.

2. The synthetic polynucleotide of claim 1, wherein the polynucleotide has at least about 90% identity to the nucleic acid sequence of SEQ ID NO:1, SEQ ID NO:4, SEQ ID NO:5, or SEQ ID NO:6.

3. The synthetic polynucleotide of claim 1, wherein the polynucleotide has at least about 95% identity to the nucleic acid sequence of SEQ ID NO:1, SEQ ID NO:4, SEQ ID NO:5, or SEQ ID NO:6.

4. The synthetic polynucleotide of claim 1, wherein SEQ ID NO:1, SEQ ID NO:4, SEQ ID NO:5, or SEQ ID NO:6 exhibits increased expression in an appropriate host relative to the expression of SEQ ID NO:3 in an appropriate host.

5. The synthetic polynucleotide of claim 3, wherein the synthetic polynucleotide having increased expression comprises a nucleic acid sequence comprising codons that have been optimized relative to the naturally occurring human methylmalonyl-CoA mutase polynucleotide sequence (SEQ ID NO:3).

6. The synthetic polynucleotide of claim 5, wherein the nucleic acid sequence has at least about 70% of less commonly used codons replaced with more commonly used codons.

7. An expression vector comprising the synthetic polynucleotide of claim 1.

8. The expression vector of claim 7, wherein the expression vector is AAV2/8-HCR-hAAT-RBG.

9. A method of treating a disease or condition mediated by methylmalonyl-CoA mutase, comprising administering to a subject in need thereof a therapeutic amount of the synthetic polynucleotide of claim 1.

10. The method of claim 9, wherein the disease or condition is methylmalonic acidemia (MMA).

11. A method of treating a disease or condition mediated by methylmalonyl-CoA mutase, comprising administering to a cell of a subject in need thereof the polynucleotide of claim 1, wherein the polynucleotide is inserted into the cell of the subject via genome editing on the cell of the subject using a nuclease selected from the group of zinc finger nucleases (ZFNs), transcription activator-like effector nucleases (TALENs), the clustered regularly interspaced short palindromic repeats (CRISPER/cas system) and meganuclease re-engineered homing endonucleases on a cell from the subject; and administering the cell to the subject.

* * * * *